US011589797B2

(12) United States Patent
    Chen

(10) Patent No.: US 11,589,797 B2
(45) Date of Patent: Feb. 28, 2023

(54) SYSTEM AND METHOD FOR NEUROTRANSMITTER MEASUREMENT

(71) Applicant: University of Mississippi Medical Center, Jackson, MS (US)

(72) Inventor: Lewis Chen, Jackson, MS (US)

(73) Assignee: University of Mississippi Medical Center, Jackson, MS (US)

( * ) Notice: Subject to any disclaimer, the term of this patent is extended or adjusted under 35 U.S.C. 154(b) by 477 days.

(21) Appl. No.: 14/293,069

(22) Filed: Jun. 2, 2014

(65) Prior Publication Data

US 2014/0357968 A1    Dec. 4, 2014

Related U.S. Application Data

(60) Provisional application No. 61/829,606, filed on May 31, 2013.

(51) Int. Cl.
    *A61B 5/00*   (2006.01)
    *A61B 5/145*  (2006.01)
    *A61B 5/11*   (2006.01)

(52) U.S. Cl.
    CPC .......... *A61B 5/4082* (2013.01); *A61B 5/1114* (2013.01); *A61B 5/14546* (2013.01); *A61B 5/7278* (2013.01)

(58) Field of Classification Search
    CPC ............................. A61B 5/4082; A61B 5/1114
    See application file for complete search history.

(56) References Cited

U.S. PATENT DOCUMENTS

2005/0099601 A1*  5/2005  MacDougall .......... A61B 3/113
                                                         351/209

OTHER PUBLICATIONS

Reilly, James L., et al. "Pharmacological treatment effects on eye movement control." Brain and cognition 68.3 (2008): 415-435.*
Chan, Florence, et al. "Deficits in saccadic eye-movement control in Parkinson's disease." Neuropsychologia 43.5 (2005): 784-796.*
(Continued)

*Primary Examiner* — Alex M Valvis
*Assistant Examiner* — Yasmeen S Warsi
(74) *Attorney, Agent, or Firm* — Stites & Harbison PLLC; Richard S. Myers, Jr.

(57) ABSTRACT

Embodiments of the presently-disclosed subject matter include methods and systems for measuring a level of a neurotransmitter in a subject. Embodiments of the present methods comprise displaying a fixation point, a reward target, and a non-reward target, and measuring one or more saccade movement parameters for reward saccades and non-reward saccades. The saccade movement parameters can include velocity, amplitude, reaction time, or a combination thereof. The present methods can further include determining a reward modulation of the subject, the reward modulation being equal to a difference between the reward and the non-reward values for a respective saccade movement parameter. Some embodiments further include identifying the subject as including a deficiency of the neurotransmitter if there is a statistically measurable difference between the reward modulation of the subject and a reference reward modulation and/or if the non-reward and the reward saccade movement parameters are statistically equivalent.

12 Claims, 23 Drawing Sheets

(56) References Cited

OTHER PUBLICATIONS

Takikawa Y1, Kawagoe R, Itoh H, Nakahara H, Hikosaka O. Modulation of saccadic eye movements by predicted reward outcome. Exp Brain Res. Jan. 2002;142(2):284-91. Epub Nov. 28, 2001.*
Amador, N., Schlag-Rey, M. & Schlag, J. (2000) Reward-predicting and reward-detecting neuronal activity in the primate supplementary eye field. J. Neurophysiol., 84, 2166-2170.
Amador, N., Schlag-Rey, M. & Schlag, J. (2004) Primate antisaccade. II. Supplementary eye field neuronal activity predicts correct performance. J. Neurophysiol., 91, 1672-1689.
Bahill, A. T., Clark, M. R., and Stark, L. (1975). The main sequence, a tool for studying human eye movements. Math Biosci. 24, 191-204.
Baloh, R. W., Sills, A. W., Kumley, W. E., and Honrubia, V. (1975). Quantitative measurement of saccade amplitude, duration, and velocity. Neurology 25, 1065-1070.
Barton, E.J. & Sparks, D.L. (2001) Saccades to remembered targets exhibit enhanced orbital position effects in monkeys. Vision Res., 41, 2393-2406.
Basso, M.A. & Sommer, M.A. (2011) Exploring the role of the substantia nigra pars reticulata in eye movements. Neuroscience, 198, 205-212.
Bray, S. and O'Doherty, J. (2007). Neural coding of reward-prediction error signals during classical conditioning with attractive faces. J. Neurophysiol. 97, 3036-3045, doi:01211.2006 [pii];10.1152/jn.01211.2006 [doi].
Bromberg-Martin, E. S. and Hikosaka, O. (2009). Midbrain dopamine neurons signal preference for advance information about upcoming rewards. Neuron 63, 119-126.
Chen, L.L. (2006) Head movements evoked by electrical stimulation in the frontal eye field of the monkey: evidence for independent eye and head control. J. Neurophysiol., 95, 3528-3542.
Chen, L.L. & Tehovnik, E.J. (2007) Cortical control of eye and head movements: integration of movements and percepts. Eur. J. Neurosci., 25, 1253-1264.
Chen, L.L. & Walton, M.M. (2005) Head movement evoked by electrical stimulation in the supplementary eye field of the rhesus monkey. J. Neurophysiol., 94, 4502-4519.
Chen, L.L. & Wise, S.P. (1995a) Neuronal activity in the supplementary eye field during acquisition of conditional oculomotor associations. J. Neurophysiol., 73, 1101-1121.
Chen, L.L. & Wise, S.P. (1995b) Supplementary eye field contrasted with the frontal eye field during acquisition of conditional oculomotor associations. J. Neurophysiol., 73, 1122-1134.
Chen, L.L. & Wise, S.P. (1996) Evolution of directional preferences in the supplementary eye field during acquisition of conditional oculomotor associations. J. Neurosci., 16, 3067-3081.
Chen, L.L. & Wise, S.P. (1997) Conditional oculomotor learning: population vectors in the supplementary eye field. J. Neurophysiol., 78, 1166-1169.
Chen, L. L., Hung, L. Y., Quinet, J., and Kosek, K. (2013). Cognitive regulation of saccadic velocity by reward prospect. Eur. J. Neurosci. 38, 2434-2444.
Collewijn, H., Erkelens, C.J. & Steinman, R.M. (1988) Binocular co-ordination of human horizontal saccadic eye movements. J. Physiol., 404, 157-182.
Collins, C.C., O'Meara, D. & Scott, A.B. (1975) Muscle tension during unrestrained human eye movements. J. Physiol., 245, 351-369.
Davis-Lopez de Carrizosa, M.A., Morado-Diaz, C.J., Miller, J.M., de la Cruz, R.R. & Pastor, A.M. (2011) Dual encoding of muscle tension and eye position by abducens motoneurons. J. Neurosci., 31, 2271-2279.
Ding, L. & Hikosaka, O. (2006) Comparison of reward modulation in the frontal eye field and caudate of the macaque. J. Neurosci., 26, 6695-6703.
Fahle, M. and Schmid, M. (1988). Naso-temporal asymmetry of visual perception and of the visual cortex. Vision Res. 28, 293-300.
Fuchs, A.F. & Robinson, D.A. (1966) A method for measuring horizontal and vertical eye movement chronically in the monkey. J. Appl. Physiol., 21, 1068-1070.
Gamlin, P.D. & Miller, J.M. (2012) Extraocular muscle motor units characterized by spike-triggered averaging in alert monkey. J. Neurosci. Meth., 204, 159-167.
Glimcher, P.W. (2011) Understanding dopamine and reinforcement learning: the dopamine reward prediction error hypothesis. Proc. Natl. Acad. Sci. USA, 108(Suppl 3), 15647-15654.
Gregorios-Pippas, L., Tobler, P. N., and Schultz, W. (2009). Short-term temporal discounting of reward value in human ventral striatum. J. Neurophysiol. 101, 1507-1523.
Haith, A.M., Reppert, T.R. & Shadmehr, R. (2012) Evidence for hyperbolic temporal discounting of reward in control of movements. J. Neurosci., 32, 11727-11736.
Hanes, D.P., Smith, M.K., Optican, L.M. & Wurtz, R.H. (2005) Recovery of saccadic dysmetria following localized lesions in monkey superior colliculus. Exp. Brain Res., 160, 312-325.
Hayden, B. Y., Parikh, P. C., Deaner, R. O., and Platt, M. L. (2007). Economic principles motivating social attention in humans. Proc. Biol. Sci. 274, 1751-1756, doi:3465J3457K7L6620 [pii];10.1098/rspb.2007.0368 [doi].
Hikosaka, O., Nakamura, K., and Nakahara, H. (2006). Basal ganglia orient eyes to reward. J. Neurophysiol. 95, 567-584.
Hikosaka, O. & Wurtz, R.H. (1983) Visual and oculomotor functions of monkey substantia nigra pars reticulata. IV. Relation of substantia nigra to superior colliculus. J. Neurophysiol., 49, 1285-1301.
Hikosaka, O. & Wurtz, R.H. (1985a) Modification of saccadic eye movements by GABA-related substances. I. Effect of muscimol and bicuculline in monkey superior colliculus. J. Neurophysiol., 53, 266-291.
Hikosaka, O. & Wurtz, R.H. (1985b) Modification of saccadic eye movements by GABA-related substances. II. Effects of muscimol in monkey substantia nigra pars reticulata. J. Neurophysiol., 53, 292-308.
Hikosaka, O., Takikawa, Y. & Kawagoe, R. (2000) Role of the basal ganglia in the control of purposive saccadic eye movements. Physiol. Rev., 80, 953-978.
Hong, S. & Hikosaka, O. (2011) Dopamine-mediated learning and switching in cortico-striatal circuit explain behavioral changes in reinforcement learning. Front. Behav. Neurosci., 5, 15.
Isoda, M. & Hikosaka, O. (2011) Cortico-basal ganglia mechanisms for overcoming innate, habitual and motivational behaviors. Eur. J. Neurosci., 33, 2058-2069.
Itoh, H., Nakahara, H., Hikosaka, O., Kawagoe, R., Takikawa, Y. & Aihara, K. (2003) Correlation of primate caudate neural activity and saccade parameters in reward-oriented behavior. J. Neurophysiol., 89, 1774-1783.
Johannesson, O. I., Asgeirsson, A. G., and Kristjansson, A. (2012). Saccade performance in the nasal and temporal hemifields. Exp. Brain Res. 219, 107-120, doi:10.1007/s00221-012-3071-2 [doi].
Judge, S.J., Richmond, B.J. & Chu, F.C. (1980) Implantation of magnetic search coils for measurement of eye position an improved method. Vision Res., 20, 535-538.
Kable, J. W. and Glimcher, P. W. (2007). The neural correlates of subjective value during intertemporal choice. Nat. Neurosci 10, 1625-1633.
Kable, J. W. and Glimcher, P. W. (2010). An "as soon as possible" effect in human intertemporal decision making behavioral evidence and neural mechanisms. J. Neurophysiol. 103, 2513-2531.
Kampe, K. K., Frith, C. D., Dolan, R. J., and Frith, U. (2001). Reward value of attractiveness and gaze. Nature 413, 589, doi:10.1038/35098149 [doi];35098149 [pii].
Kato, M., Miyashita, N., Hikosaka, O., Matsumura, M., Usui, S. & Kori, A. (1995) Eye movements in monkeys with local dopamine depletion in the caudate nucleus. I. Deficits in spontaneous saccades. J. Neurosci., 15, 912-927.
Kawagoe, R., Takikawa, Y. & Hikosaka, O. (1998) Expectation of reward modulates cognitive signals in the basal ganglia. Nat. Neurosci., 1, 411-416.

(56) References Cited

OTHER PUBLICATIONS

Kawagoe, R., Takikawa, Y. & Hikosaka, O. (2004) Reward-predicting activity of dopamine and caudate neurons—a possible mechanism of motivational control of saccadic eye movement. J. Neurophysiol., 91, 1013-1024.

Kobayashi, S. and Schultz, W. (2008). Influence of reward delays on responses of dopamine neurons. J. Neurosci. 28, 7837-7846.

Koene, A.R. & Erkelens, C.J. (2002) Cause of kinematic differences during centrifugal and centripetal saccades. Vision Res., 42, 1797-1808.

Kustov, A.A. & Robinson, D.L. (1995) Modified saccades evoked by stimulation of the macaque superior colliculus account for properties of the resettable integrator. J. Neurophysiol., 73, 1724 1728.

Lee, C., Rohrer, W.H. & Sparks, D.L. (1988) Population coding of saccadic eye movements by neurons in the superior colliculus. Nature, 332, 357-360.

Lefevre, P., Quaia, C. & Optican, L.M. (1998) Distributed model of control of saccades by superior colliculus and cerebellum. Neural Networks, 11, 1175-1190.

Levy, D.J. & Glimcher, P.W. (2012) The root of all value: a neural common currency for choice. Curr. Opin. Neurobiol., 22, 1027-1038.

Louie, K., Grattan, L. E., and Glimcher, P. W. (2011). Reward value-based gain control: divisive normalization in parietal cortex. J. Neurosci 31, 10627-10639, doi:31/29/10627 [pii];10.1523/JNEUROSCI.1237-11.2011 [doi].

Madelain, L., Paeye, C., and Wallman, J. (2011). Modification of saccadic gain by reinforcement. J. Neurophysiol. 106, 219-232, doi:jn.01094.2009 [pii];10.1152/jn.01094.2009 [doi].

Marino, R.A. & Munoz, D.P. (2009) The effects of bottom-up target luminance and top-down spatial target predictability on saccadic reaction times. Exp. Brain Res., 197, 321-335.

Marino, R.A., Levy, R., Boehnke, S., White, B.J., Itti, L. & Munoz, D.P. (2012) Linking visual response properties in the superior colliculus to saccade behavior. Eur. J. Neurosci., 35, 1738-1752.

Matsumoto, M. & Hikosaka, O. (2009) Two types of dopamine neuron distinctly convey positive and negative motivational signals. Nature, 459, 837-841.

May, P.J. (2006) The mammalian superior colliculus: laminar structure and connections. Prog. Brain Res., 151, 321-378.

McClure, S. M., Ericson, K. M., Laibson, D. I., Loewenstein, G., and Cohen, J. D. (2007). Time discounting for primary rewards. J. Neurosci. 27, 5796-5804.

Meyer, G.A., McCulloch, A.D. & Lieber, R.L. (2011) A nonlinear model of passive muscle viscosity. J. Biomech. Eng., 133, Sep. 10, 2007.

Miller, J.M., Davison, R.C. & Gamlin, P.D. (2011) Motor nucleus activity fails to predict extraocular muscle forces in ocular convergence. J. Neurophysiol., 105, 2863-2873.

Nakamura, K. & Hikosaka, O. (2006) Role of dopamine in the primate caudate nucleus in reward modulation of saccades. J. Neurosci., 26, 5360-5369.

Nichols, M.J. & Sparks, D.L. (1995) Nonstationary properties of the saccadic system: new constraints on models of saccadic control. J. Neurophysiol., 73, 431-435.

Nichols, M.J. & Sparks, D.L. (1996) Component stretching during oblique stimulation-evoked saccades: the role of the superior colliculus. J. Neurophysiol., 76, 582-600.

Van Opstal, A.J. & van Gisbergen, J.A. (1990) Role of monkey superior colliculus in saccade averaging. Exp. Brain Res., 79, 143-149.

Van Opstal, A.J., Hepp, K., Suzuki, Y. & Henn, V. (1995) Influence of eye position on activity in monkey superior colliculus. J. Neurophysiol., 74, 1593-1610.

Optican, L.M. & Quaia, C. (2002) Distributed model of collicular and cerebellar function during saccades. Ann. NY Acad. Sci., 956, 164-177.

Pare, M. & Munoz, D.P. (1996) Saccadic reaction time in the monkey: advanced preparation of oculomotor programs is primarily responsible for express saccade occurrence. J. Neurophysiol., 76, 3666-3681.

Pasupathy, A. and Miller, E. K. (2005). Different time courses of learning-related activity in the prefrontal cortex and striatum. Nature 433, 873-876.

Pelisson, D. & Prablanc, C. (1988) Kinematics of centrifugal and centripetal saccadic eye movements in man. Vision Res., 28, 87-94.

Pfann, K.D., Keller, E.L. & Miller, J.M. (1995) New models of the oculomotor mechanics based on data obtained with chronic muscle force transducers. Ann. Biomed. Eng., 23, 346-358.

Quaia, C. & Optican, L.M. (1997) Model with distributed vectorial premotor bursters accounts for the component stretching of oblique saccades. J. Neurophysiol., 78, 1120-1134.

Quaia, C., Lefevre, P. & Optican, L.M. (1999) Model of the control of saccades by superior colliculus and cerebellum. J. Neurophysiol., 82, 999-1018.

Ratal, R., Henik, A., and Smith, J. (1991). Extrageniculate contributions to reflex visual orienting in normal humans: a temporal hemifield advantage. J. Cogn Neurosci. 3, 322-328.

Robinson, D. A. (1964). The mechanics of human saccadic eye movment. J. Physiol 174, 245-264.

Rodriguez, C. A., Turner, B. M., and McClure, S. M. (2014). Intertemporal choice as discounted value accumulation. PLoS. One. 9, e90138.

Sato, M. & Hikosaka, O. (2002) Role of primate substantia nigra pars reticulata in reward-oriented saccadic eye movement. J. Neurosci., 22, 2363-2373.

Schiller, P.H., True, S.D. & Conway, J.L. (1980) Deficits in eye movements following frontal eye-field and superior colliculus ablations. J. Neurophysiol., 44, 1175-1189.

Schultz, W. (2002) Getting formal with dopamine and reward. Neuron, 36, 241-263.

Schultz, W. (2013). Updating dopamine reward signals. Curr. Opin. Neurobiol. 23, 229-238.

Schultz, W. (2006) Behavioral theories and the neurophysiology of reward. Annu. Rev. Psychol., 57, 87-115.

Schultz, W., Dayan, P. & Montague, P.R. (1997) A neural substrate of prediction and reward. Science, 275, 1593-1599.

Shadmehr, R., Orban de Xivry, J.J., Xu-Wilson, M. & Shih, T.Y. (2010) Temporal discounting of reward and the cost of time in motor control. J. Neurosci., 30, 10507-10516.

Shadmehr, R. (2010). Control of movements and temporal discounting of reward. Curr. Opin. Neurobiol. 20, 726-730, doi:S0959-4388(10)00137-6 [pii];10.1016/j.conb.2010.08.017 [doi].

Soetedjo, R., Kaneko, C.R. & Fuchs, A.F. (2002) Evidence that the superior colliculus participates in the feedback control of saccadic eye movements. J. Neurophysiol., 87, 679-695.

Sommer, M.A. & Wurtz, R.H. (2008) Brain circuits for the internal monitoring of movements. Annu. Rev. Neurosci., 31, 317-338.

Sparks, D.L. (2002) The brainstem control of saccadic eye movements. Nat. Rev. Neurosci., 3, 952-964.

Stanford, T.R. & Sparks, D.L. (1994) Systematic errors for saccades to remembered targets: evidence for a dissociation between saccade metrics and activity in the superior colliculus. Vision Res., 34, 93-106.

Sylvester, R., Josephs, O., Driver, J., and Rees, G. (2007). Visual fMRI responses in human superior colliculus show a temporal-nasal asymmetry that is absent in lateral geniculate and visual cortex. J. Neurophysiol. 97, 1495-1502.

Takikawa, Y., Kawagoe, R., Itoh, H., Nakahara, H. & Hikosaka, O. (2002) Modulation of saccadic eye movements by predicted reward outcome. Exp. Brain Res., 142, 284-291.

Tanaka, M. (2007) Spatiotemporal properties of eye position signals in the primate central thalamus. Cereb. Cortex, 17, 1504-1515.

Tobler, P.N., Fiorillo, C.D. & Schultz, W. (2005) Adaptive coding of reward value by dopamine neurons. Science, 307, 1642-1645.

Van den Bos, W. and McClure, S. M. (2013). Towards a general model of temporal discounting. J. Exp. Anal. Behav. 99, 58-73.

Van der Vegt, J. P., Hulme, O. J., Zittel, S., Madsen, K. H., Weiss, M. M., Buhmann, C., Bloem, B. R., Munchau, A., and Siebner, H.

(56) References Cited

OTHER PUBLICATIONS

R. (2013). Attenuated neural response to gamble outcomes in drug-naive patients with Parkinson's disease. Brain 136, 1192-1203.

Van Opstal, A. J., Hepp, K., Suzuki, Y., and Henn, V. (1995). Influence of eye position on activity in monkey superior colliculus. J. Neurophysiol. 74, 1593-1610.

Van Opstal, A. J. and van Gisbergen, J. A. (1990). Role of monkey superior colliculus in saccade averaging. Exp. Brain Res. 79, 143-149.

Watanabe, M. & Munoz, D.P. (2011) Probing basal ganglia functions by saccade eye movements. Eur. J. Neurosci., 33, 2070-2090.

White, B.J., Theeuwes, J. & Munoz, D.P. (2012) Interaction between visual- and goal-related neuronal signals on the trajectories of saccadic eye movements. J. Cognitive Neurosci., 24, 707-717.

Wurtz, R.H. & Goldberg, M.E. (1972) Activity of superior colliculus in behaving monkey. IV. Effects of lesions on eye movements. J. Neurophysiol., 35, 587-596.

Xu-Wilson, M., Zee, D. S., and Shadmehr, R. (2009). The intrinsic value of visual information affects saccade velocities. Exp. Brain Res. 196, 475-481.

Yasuda, M., Yamamoto, S. & Hikosaka, O. (2012) Robust representation of stable object values in the oculomotor Basal Ganglia. J. Neurosci., 32, 16917-16932.

Chen LL, Chen YM, Zhou W, and Mustain WD: Monetary reward speeds up voluntary saccades; Frontiers in Integrative Neuroscience. 2014 doi: 10.3389/fnint.2014.00048.

\* cited by examiner

Peak velocity of 9.5-10.0° saccades

SYSTEM AND METHOD FOR NEUROTRANSMITTER MEASUREMENT

RELATED APPLICATION

This application claims priority from U.S. Provisional Patent Application No. 61/829,606, filed May 31, 2013, the entire disclosure of which is incorporated herein by this reference.

GOVERNMENT INTEREST

The invention described herein was made with government support under Grant Number EY016710 awarded by the National Institutes of Health. The government has certain rights in the invention.

TECHNICAL FIELD

The presently-disclosed subject matter relates to methods and systems for measuring the level of a neurotransmitter in a subject. In particular, the presently-disclosed subject matter relates to methods and systems that utilize saccadic eye movement parameters of a subject to measure dopamine levels.

INTRODUCTION

Measurement of neurotransmitters and compounds associated with neurons is typically an invasive process. Many known methods rely on the collection of brain tissue or other samples to measure levels of neurotransmitters and other associated compounds. These methods are therefore highly invasive, time-consuming, expensive, and require personnel having a high degree of skill.

Measuring the levels of neurotransmitters in a subject can be useful for diagnosing or tracking the progress of a disease or condition. Parkinson's disease is an example of such a neurodegenerative condition, and is generally known to cause the depletion of dopamine, which is brought about by the death of dopamine-generating cells in the substantia nigra. Therefore, in the case of Parkinson's disease, measuring levels of dopamine can be useful for diagnosing a subject, tracking the progress of the disease or condition, or determining how to administer or modify treatment.

Hence, there remains a need for a noninvasive systems and methods for measuring the level of neurotransmitters, brain activity, and other compounds associated with neurons. Additionally, there remains a need for systems and methods that are cost-effective, relatively quick, and do not require highly trained personnel.

top; second: bottom) and (B) the population averages of reward modulation across subjects. $P<0.05*$; $P<0.01$; $P<0.001*$. C.I.: confidence interval.

Figure 14A:
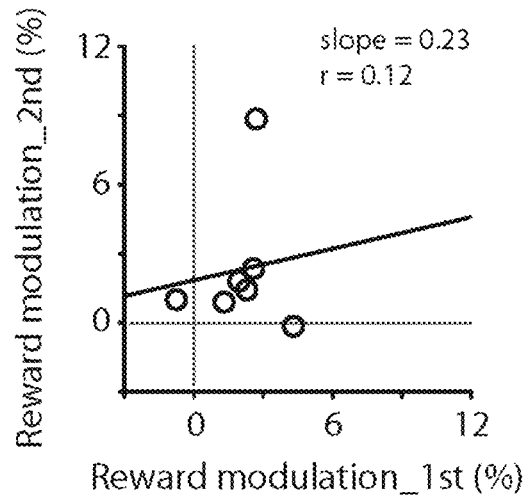
Figure 14B:
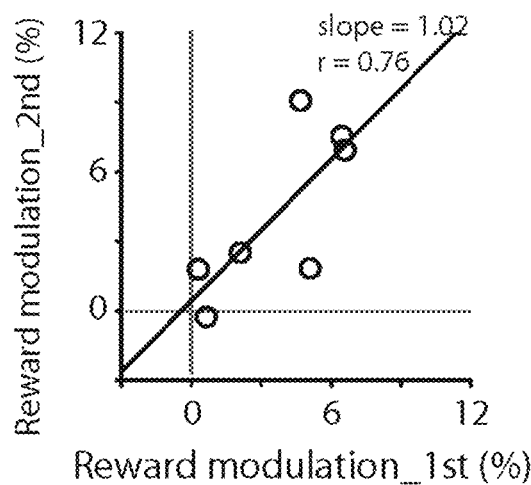

FIG. 14 includes graphs showing the correlation of reward modulation between the first (abscissa) and second (ordinate) tests separating for leftward (A) and rightward (B) saccades. Pearson correlation, r=0.76, P<0.05.

FIG. 15 graphs of the stability of the nasal-temporal velocity asymmetry (NTVA) of unrewarded saccades showing (A) peak velocity data obtained from 9.5-10.0° unrewarded saccades during the first test of each subject (nasal saccades: open bars; temporal saccades: filled bars), (B) the NTVA of unrewarded saccades ($NTVA_{UR}$) separated for the first and second tests, positive value indicating the velocity by which temporal saccades were faster than nasal saccades, and vice versa, and (C) the correlation of NTVA between the first (abscissa) and second (ordinate) tests.

FIG. 16 includes graphs showing (A,B) reward modulation (RM; ordinate) versus individual subjects' peak velocities (abscissa), (C,D) reward modulation versus the nasal-temporal velocity asymmetry (NTVA; abscissa), and (E,F) differential reward modulation between temporal and nasal saccades versus the nasal-temporal velocity asymmetry.

Figure 17A:
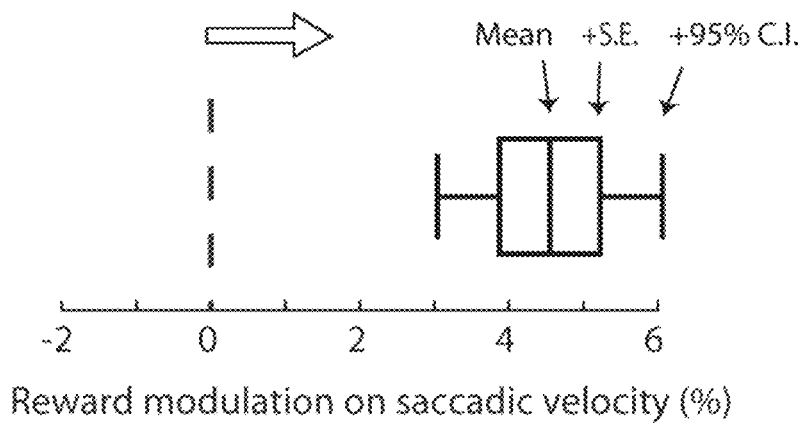
Figure 17B:
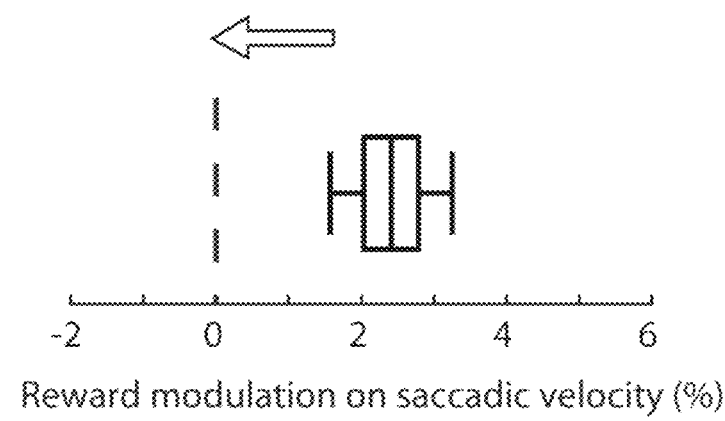

FIG. 17 includes graphs showing percent reward modulation (RM %, dopamine sensitivity) in healthy participants (N=11) for (A) rightward saccades and (B) leftward saccades, wherein each box plot depicts the mean, ±S.E.M., and ±95% confidence interval.

Figure 18A:
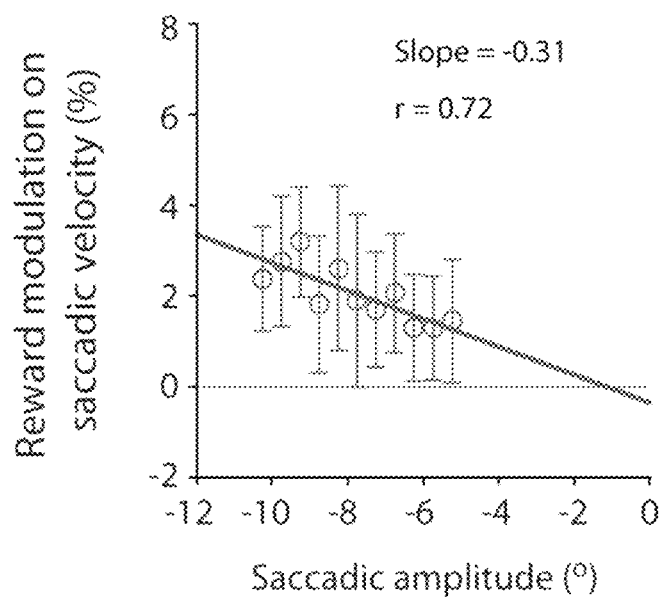
Figure 18B:
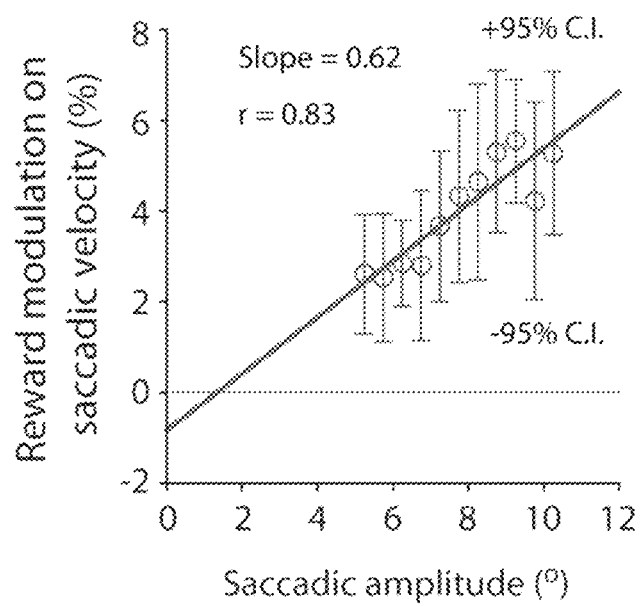

FIG. 18 includes graphs showing percent reward modulation (RM %, dopamine sensitivity) as a function of saccadic amplitude (abscissa) in healthy participants (N=11) for (A) leftward saccades and (B) rightward saccades, wherein each data point (open circle) represents the averaged RM % per amplitude bin (width=0.5°) across the subjects, and the vertical bar corresponds to the ±95% confidence interval for each amplitude bin.

Figure 19:
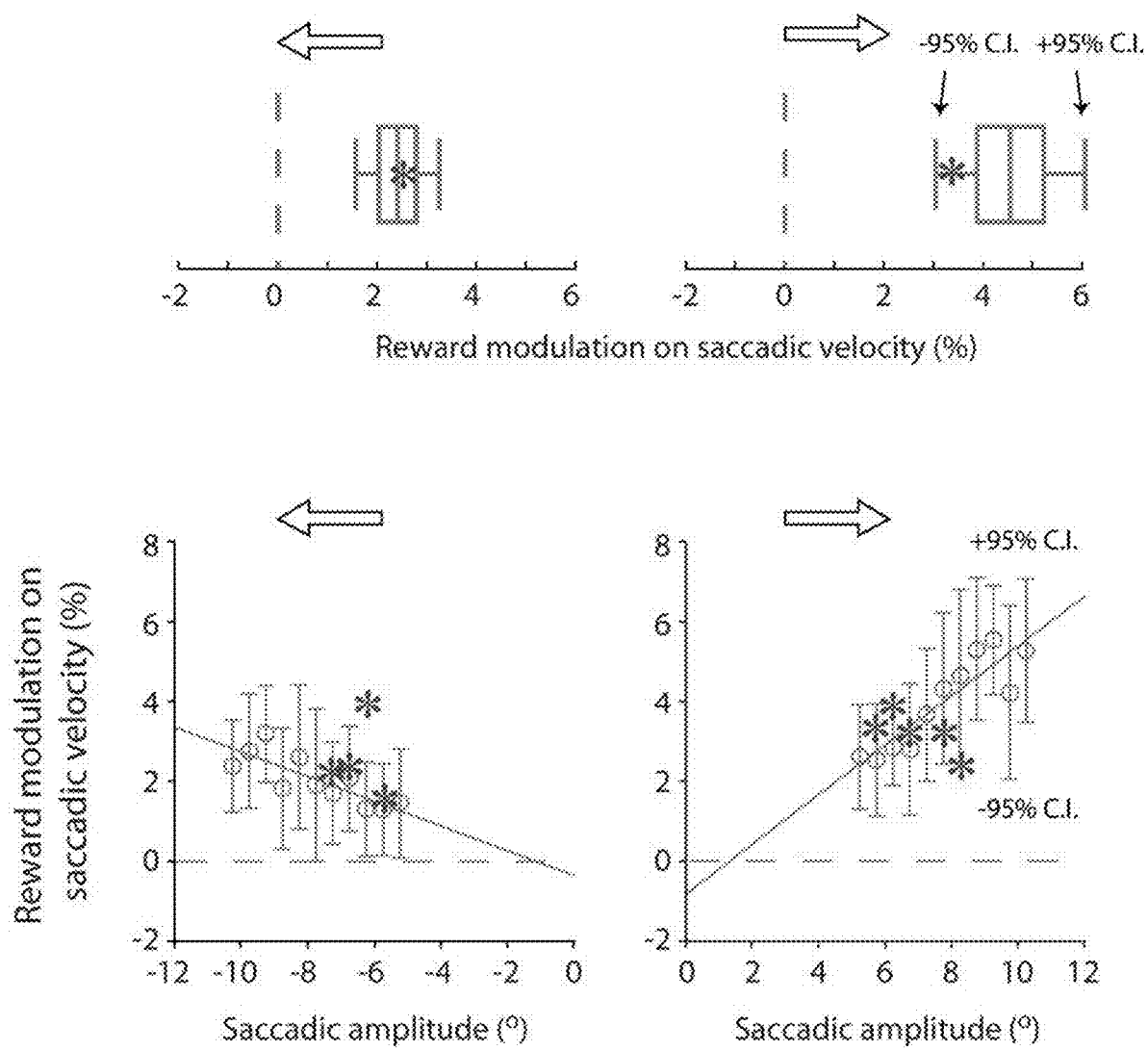

FIG. 19 includes graphs showing percent reward modulation (dopamine sensitivity) of a patient who was diagnosed with non-Parkinsonic essential tremor (asterisks) superimposed on top of the healthy participants' data depicted in FIGS. 17 and 18.

Figure 20:
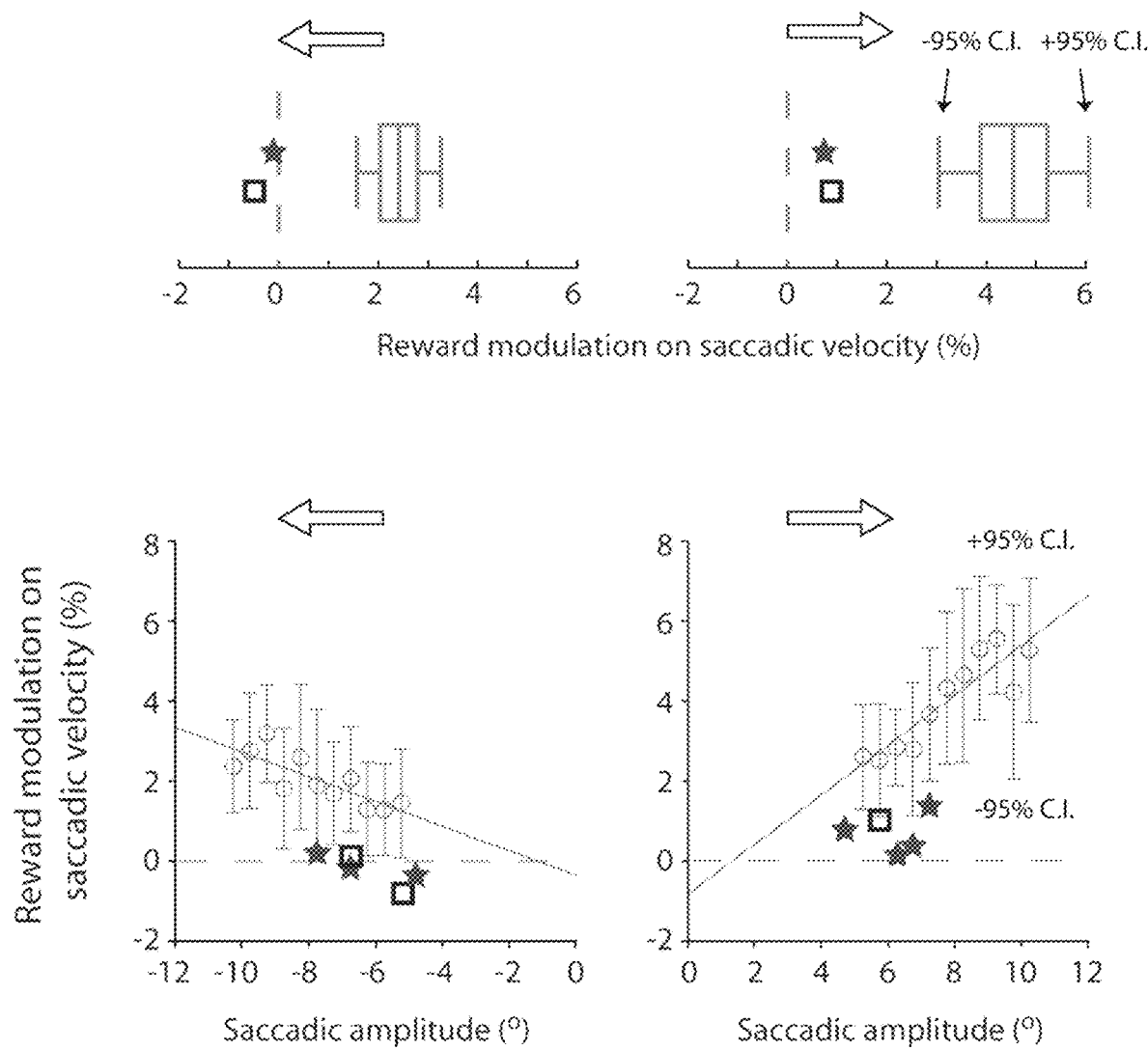

FIG. 20 includes graphs showing percent reward modulation (dopamine sensitivity) of two Parkinson's disease (PD) patients (filled star and open square) superimposed on top of the healthy participants' data depicted in FIGS. 17 and 18.

Figure 21:
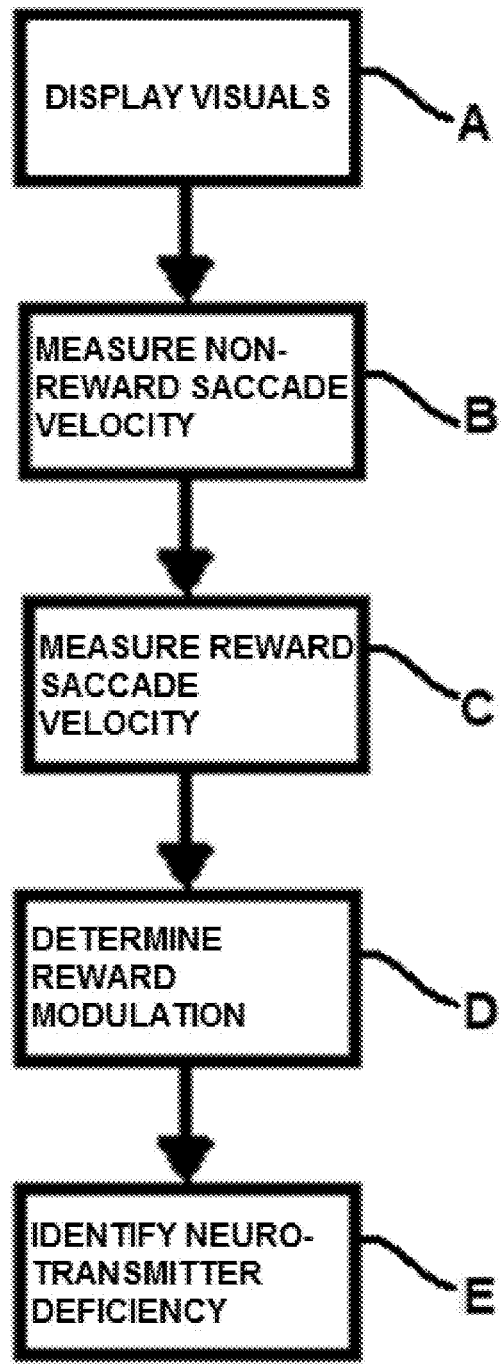

FIG. 21 includes a flow diagram showing an exemplary method of measuring a level of a neurotransmitter in a subject in accordance with the presently-disclosed subject matter.

Figure 22:
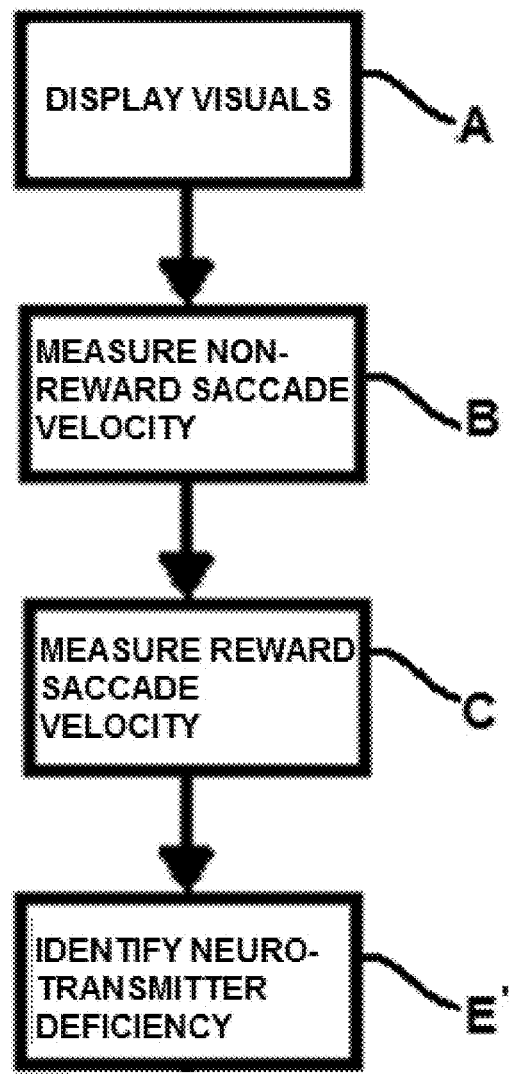

FIG. 22 includes a flow diagram showing another exemplary method of measuring a level of a neurotransmitter in a subject in accordance with the presently-disclosed subject matter.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes methods and system for measuring a level of a neurotransmitter in a subject. The present methods and system can measure a level of a neurotransmitter by correlating the level of the neurotransmitter to a one or more saccadic eye movement parameters that are measured during reward and non-reward conditional task stimulations. In some embodiments of the present methods and systems, the measured saccadic eye movement parameters are selected from saccadic velocity, saccadic amplitude (gain), saccadic reaction time (latency), and combinations thereof that are produced by the subject. The presently-disclosed methods, which include measuring saccadic movement parameters under different conditions, can be implemented without needing to rely on known, invasive techniques for measuring the level of a neurotransmitter in a subject.

Measuring the level of a neurotransmitter can include identifying whether the subject includes a deficiency of a neurotransmitter, a healthy (normal) level of a neurotransmitter, and/or an excess of a neurotransmitter. As used herein, a "healthy level" of a neurotransmitter refers to a level of a neurotransmitter that a healthy subject would have. A healthy level can refer to a level that falls within a range that is acceptable for healthy subjects. The term healthy subject can therefore include one or more subjects that do not have a disease or condition that otherwise may affect the level of the neurotransmitter, that do not display the symptoms associated with a disease or condition that otherwise affects the level of the neurotransmitter, that have undergone treatment for a neurodegenerative condition, that are known to be healthy, or a combination thereof. Thus, a healthy level of a neurotransmitter refers to a level of a neurotransmitter that allows the subject to have normal, healthy biological functioning. The terms deficiency and excess describe a level of a neurotransmitter in a subject in comparison to a healthy level of the neurotransmitter.

The term "subject" is inclusive of both animal and human subjects. Veterinary uses are provided in accordance with the presently disclosed subject matter and the presently-disclosed subject matter provides methods for determining the health of a mammals such as cattle, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the monitoring of birds, including the monitoring of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the monitoring of livestock, including, but not limited to, domesticated swine, ruminants, ungulates, horses, poultry, and the like.

The terms "saccade," "saccadic eye movement," and the like are used herein to refer to a rapid angular rotation of the eyes to shift the line of sight and bring an object of interest into focus. This process is often utilized to shift a subject's attention and/or to prepare the subject for movements. Hence, saccadic movement parameters, such as saccadic velocity, saccadic amplitude, and/or saccadic reaction time, can offer an early indication of sensorimotor function. The saccade can span between two visuals, wherein the visual that the eye initially focuses on is referred to herein as a "fixation point," and the visual that the eye moves to during a saccade is referred to herein as a "target."

The target visual can be either a reward target or a non-reward target. There is no particular limitation to the visuals that can be used. In some instances the fixation point is any visual that the subject can initially focus on and that can serve as the starting location of a saccade, whereas the target can be another visual the subject can look to in order to perform the saccade. Thus, a saccade can include the rotation of the eyes of a subject from an initial fixation point to a final target. Exemplary targets can include images that induce monetary, food, absence of pain, and social recognition stimuli. The term "reward target" refers to a target is intended to elicit or is associated with a positive mental response, whereas the term "non-reward target" refers to a target that is intended to elicit or is associated with a neutral and/or negative mental response. In this respect, saccades can be classified as reward saccades, which span between a fixation point and a reward target, or non-reward saccades, which span between a fixation point and a non-reward target.

The saccades discussed herein are distinguishable from eye pursuits (i.e., following one object) and do not include involuntary movements such as nystagmus and vestibule-ocular reflexive eye counter-rotation. Each of these types of movements are segregated and controlled by different neural mechanisms in the brain.

Saccades can be varied and characterized in several ways. Saccades include an initial starting point, and this starting point can be varied by varying the location of the fixation point relative to the eye of the subject. The direction of saccades can also be varied by varying the location of a target relative to a fixation point (i.e., target amplitude). With respect to direction, in some instances the saccades described herein can be centripetal (CP) saccades that cause the eye to move toward center of a subject's field of view and/or generally towards their nose, and in some instances the saccades described herein can be centrifugal (CF) saccades that cause the eye to move toward the periphery of a subject's field of view and/or generally away from their nose.

Saccade movement can be characterized in terms of the velocity of the saccade. The saccades described herein can include saccadic eye movements having velocities of 200 deg/sec or less, 400 deg/sec or less, 600 deg/sec or less, 800 deg/sec or less, 1,000 deg/sec or less, or 1,200 deg/sec or less. In some instances saccadic velocities are correlated with saccadic amplitude, and saccadic velocity increases/deceases with increasing/decreasing saccadic amplitude, and vice versa. In some instances saccades can include velocities as low as 20 deg/sec. In other embodiments saccades can be characterized in terms of the acceleration (i.e., double derivative of position) of the saccade.

Saccade movement can also be characterized in terms of the amplitude of the saccade. Saccadic amplitude is a measure of the total saccadic eye movement displacement during a saccade. Saccades include amplitudes that can be altered by changing the distance of a fixation point and a target, but saccadic amplitude is not necessarily equivalent of the target amplitude (e.g., the displacement between a fixation point and a target visual). Saccadic amplitude can be larger than, equal to, or smaller than the target amplitude. Thus, the term "saccadic gain" can be used to quantify the ratio of saccadic amplitude over target amplitude.

Saccade movement can also be characterized in terms of the reaction time of the saccade. Saccadic reaction time is a measure of the response time before a saccade is made to a given target. Saccadic response time varies significantly from task to task.

Some embodiments of the presently-disclosed subject matter include methods for measuring if a subject includes a deficiency of a neurotransmitter. The methods can include displaying to the subject a fixation point, a reward target, and, optionally, a non-reward target, which can be collectively referred to as "visuals" herein; measuring one or more reward saccade movement parameters (e.g., velocity, amplitude, reaction time) of the subject from the fixation point to the reward target; and identifying the subject as including a deficiency of the neurotransmitter if there is a statistically measurable difference between the reward saccade movement parameter(s) of the subject and reference reward saccade movement parameter(s).

In other words, one or more saccade movement parameters are measured during reward and, optionally, non-reward saccades. The one or more saccade movement parameters during the reward saccade can be compared to non-reward saccade movement parameters of the subject, reference values of the saccade movement parameters, and the like to measure a level of a neurotransmitter in a subject. The present methods utilize one or more saccade movement parameters, including velocity, amplitude, and reaction time, either separately or collectively in order to measure the level of the neurotransmitter in the subject.

In other embodiments, there are further provided steps of measuring one or more non-reward saccade movement parameters (e.g., velocity, amplitude, reaction time) of the subject from the fixation point to the non-reward target, and determining a reward modulation for each of the measured saccade movement parameters. Reward modulations are equal to a difference between reward and non-reward values for each respective saccade movement parameter (e.g., reward velocity minus non-reward velocity). The determining step then includes, after calculating the reward modulations for each of the measured saccade movement parameters, identifying a subject as including a deficiency of the neurotransmitter if there is a statistically measurable difference between the reward modulation of the subject and a reference reward modulation. Reward modulation can be used to measure how saccadic movement parameters vary in response to reward targets and non-reward targets.

The term "reference" as used herein describes that a certain value is that associated with one or more particular subjects. A reference saccade movement parameter can be a reference saccade movement parameter of the subject before contracting a disease or condition in response. The reference saccade movement parameter can also be one from one or more subject known to be healthy. For instance, a reference saccadic movement parameter (e.g., velocity) can be a saccadic movement parameter (e.g., velocity) of one or more healthy subjects, and a reference reward modulation can refer to reward modulation of one or more healthy subjects. The reference reward modulation can be a reward modulation of one healthy subject, or can be an average of the reward modulation of a plurality of healthy subjects. Upon reviewing the description herein, those of ordinary skill will appreciate other reference saccade movement parameters that can be utilized to measure neurotransmitter levels, diagnose a subject, or the like.

The presently-disclosed methods can also monitor clinical regimens prescribed for the treatment of abnormal neurotransmitter levels. Similarly, embodied methods may also be utilized to monitor the progress of a disease or condition, monitor the effectiveness of a treatment course, or the like. Furthermore, in some embodiments the present methods and systems can measure neurotransmitter levels in about 1 minute to 15 minutes, and in some embodiments in about 10 to about 15 minutes, which is advantageous over other known methods that require more time consuming lab work in order to measure neurotransmitter levels.

The term "statistically measurable difference" is used herein to refer to a quantifiable difference between two or more values. In some embodiments there will be a statistically measureable difference between two values depending on one or more of the number of standard deviations, standard error of the mean, or the like that the two values from each other. Similarly, a value that is "statistically lower" or "statistically greater" than a reference value refers to a value that is lower or higher than the reference value by a statistically significant amount. Likewise, a value that is "statistically equivalent to" another reference value is a value that does not differ from the reference value by a statistically significant amount.

In specific embodiments a statistically measureable difference and/or statistically significant amount can correspond to values that deviates from each other by 0.5, 1, 2, or 3 standard deviations and/or the standard error of the mean. Furthermore, in other embodiments a statistically measureable difference and/or statistically significant amount will be ascertained if a value (e.g., reward velocity) has a p-value of about 0.01 or less, 0.02 or less, 0.03 or less, 0.04 or less, 0.05 or less, 0.06 or less, 0.07 or less, 0.08 or less, 0.09 or less, or 0.10 or less relative to another value (e.g., reference reward velocity).

Embodiments of the presently-disclosed subject matter therefore include methods for measuring if a subject includes a deficiency of a neurotransmitter. As shown in FIG. 21, in some embodiments the methods comprise (A) displaying to the subject a fixation point, a reward target, and a non-reward target, which can collectively be referred to herein as visual. Then, the method includes (B) measuring a non-reward saccade velocity of the subject from the fixation point to the non-reward target, and also includes (C) measuring a reward saccade velocity of the subject from the fixation point to the reward target. Next, in some methods there is provided a step of (D) determining a velocity reward modulation of the subject, the velocity reward modulation being equal to a difference between the reward saccade velocity and a non-reward velocity. Then, after the velocity reward modulation of the subject has been determined, in some embodiments the subject can be (E) identified as including a deficiency of the neurotransmitter if there is a statistically measurable difference between the velocity reward modulation of the subject and a reference velocity reward modulation.

In this regard, embodiments of the present methods are capable of dissociating the modulation of saccadic velocity from saccadic amplitude, permitting the velocity modulation to be evaluated independently of saccadic amplitude and without sacrificing the amplitude sensitivity. In some embodiments the present methods and system dissociate modulation of saccadic velocity due to the presence or absence of rewards from saccadic amplitude. The present inventors have shown that, in some instances, reward modulation as a function of initial eye position can include a substantially linear correlation with saccadic amplitude, resulting in a systematic enhancement of saccadic velocity as saccadic amplitude increases.

In some embodiments of the present methods for measuring a level of a neurotransmitter, the reward saccade and the non-reward saccade include a predetermined amplitude. By virtue of having the same predetermined amplitude, the amplitude variable can be eliminated when comparing a reward saccade to a non-reward saccade. In some instances a reference saccade velocity and/or reference velocity reward modulation can be measured from one or more reference saccades that have the same predetermined amplitude as the reward saccade and/or non-reward saccade. In some embodiments the predetermined amplitude can be about 1, 2, 3, 4, 5, 6, 7, 8, 9, or 10 degrees or more. In other embodiment the predetermined amplitude is about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, or 180 degrees.

In some instances the neurotransmitter being measured can increase the velocity of a saccade, and in some embodiments a subject is identified as including a deficiency of a neurotransmitter if the reward modulation of the subject is statistically lower than the reference reward modulation for one or more saccadic movement parameters. In other embodiments a subject can be identified as including an excess of the neurotransmitter if the reward modulation of the subject is statistically greater than the reference reward modulation for one or more saccadic movement parameters. For instance, and without being bound by theory or mechanism, in some instances saccadic velocity is increased by dopamine-associated reward signals from the basal ganglia. Given that dopamine is a neurotransmitter that is involved in the regulation of reward value, and thus reward-associated sensorimotor processing, the present inventors have found a correlation between reward motivated saccadic eye movements and functional dopamine levels.

In some embodiments, amplitude is the saccadic movement parameter utilized to measure neurotransmitter levels. In such embodiments, rewarded and non-reward saccadic amplitudes for the same (pre-determined) target amplitudes can be measured, where the target amplitudes can be set to predetermined values of about 1, 2, 3, 4, 5, 6, 7, 8, 9, 10, 11, 12, 13, 14, 15, 16, 17, 18, 19, 20, 25, 30, 35, 40, 45, 50, 55, 60, 70, 80, 90, 100, 110, 120, 130, 140, 150, 160, 170, or 180 degrees. Therefore, in some embodiments a method is provided that comprises (A) displaying to the subject a fixation point, a reward target, and a non-reward target, (B) measuring a non-reward saccade amplitude of the subject from the fixation point to the non-reward target, and (C) measuring a reward saccade amplitude of the subject from the fixation point to the reward target. Next, in some methods there is provided a step of (D) determining a amplitude reward modulation of the subject, the amplitude reward modulation being equal to a difference between the reward saccade amplitude and a non-reward amplitude. Then, after the amplitude reward modulation of the subject has been determined, in some embodiments the subject can be (E) identified as including a deficiency of the neurotransmitter if there is a statistically measurable difference between the amplitude reward modulation of the subject and a reference amplitude reward modulation. In some instances neurotransmitter (e.g., dopamine) levels are correlated with amplitude reward modulation, and, for example, amplitude reward modulation increases as dopamine levels increase, and vice versa.

In some embodiments, reaction time is the saccadic movement parameter utilized to measure neurotransmitter levels. In such embodiments, rewarded and non-reward saccadic reaction times for the same (pre-determined) target amplitudes can be measured, where the target amplitudes can be set to predetermined values of about 1, 2, 3, 4, 5, 6, 7, 8, 9, 10, 11, 12, 13, 14, 15, 16, 17, 18, 19, 20, 25, 30, 35, 40, 45, 50, 55, 60, 70, 80, 90, 100, 110, 120, 130, 140, 150, 160, 170, or 180 degrees. Therefore, in some embodiments a method is provided that comprises (A) displaying to the subject a fixation point, a reward target, and a non-reward target, (B) measuring a non-reward saccade reaction time of the subject from the fixation point to the non-reward target, and (C) measuring a reward saccade reaction time of the subject from the fixation point to the reward target. Next, in some methods there is provided a step of (D) determining a reaction time reward modulation of the subject, the reaction time reward modulation being equal to a difference between the reward saccade reaction time and a non-reward reaction time. Then, after the reaction time reward modulation of the subject has been determined, in some embodiments the subject can be (E) identified as including a deficiency of the neurotransmitter if there is a statistically measurable difference between the reaction time reward modulation of the subject and a reference reaction time reward modulation. In some instances neurotransmitter (e.g., dopamine) levels are correlated with reaction time reward modulation, and, for example, reaction time reward modulation increases as dopamine levels increase, and vice versa.

Furthermore, the presently-disclosed subject matter includes methods for diagnosing a subject with a neurodegenerative condition based on, at least in part, whether the subject includes a deficiency and/or excess of a particular neurotransmitter. The present methods for measuring a level of a neurotransmitter can therefore further comprise diagnosing the subject with a neurodegenerative condition if the subject includes the deficiency of the neurotransmitter. In certain embodiments the neurotransmitter includes dopamine and the neurodegenerative condition includes Parkinson's disease. In other embodiments the neurodegenerative condition can be selected from dementia, Alzheimer's disease (AD), Frontotemporal dementia (FTD), Parkinson Disease Dementia (PDD), and/or Lewy Body Dementia (LBD).

The terms "diagnosing" and "diagnosis" as used herein refer to methods by which the skilled artisan can estimate and even determine whether or not a subject is suffering from a given disease or condition. Diagnosis is inclusive of "prognosis" or "prognosticating", as it is important to know the relative risk associated with particular conditions in order to plan the most effective therapy. If an accurate prognosis can be made, appropriate therapy, and in some instances less severe therapy or more effective therapy, for the patient can be chosen. In some embodiments of the presently disclosed subject matter, a method includes identifying a subject as having Parkinson's disease if the reward modulation is statistically lower than a reference reward modulation.

Further still, some embodiments of methods further comprise administering a composition for treating Parkinson's disease if the subject is diagnosed as having Parkinson's disease. In some embodiments the composition is selected from, but is not limited to, carbidopa, levodopa, dopamine agonists, such as pramipexole, ropinirole, rotigotine, bromocriptine, and apomorphine, monoamine oxidase (MAO-B) inhibitors, such as selegiline and rasagiline, catechol O-methyltransferase (COMT) inhibitors, such as entacapone and tolcapone, anticholinergics, such as benztropine and trihexyphenidyl, benztropine mesylate, procyclidine, amantadine, and rivastigmine tartrate. Alternatively or additionally, methods provide that other treatments for Parkinson's disease can be administered to diagnosed subjects, including surgical treatments, such as deep brain stimulation, and the like.

As discussed herein, in some embodiments the displaying step is performed with a virtual reality headset. In some embodiments one or more of the measuring steps are performed with a camera configured to track one or more saccade movement parameters. In some embodiments, in the identifying step, a processor executing a software program determines if there is the statistically measurable difference between the reward modulation of the subject and the reference reward modulation.

The presently-disclosed methods for measuring the level of a neurotransmitter in a subject can be modified to meet the needs of a particular situation. For instance, as shown in FIG. 22, in some embodiments the method comprises (A) displaying to the subject a fixation point, a reward target, and a non-reward target, (B) measuring a non-reward saccade movement parameter (e.g., velocity) of the subject from the fixation point to the non-reward target, (C) measuring a reward saccade movement parameter (e.g., velocity) of the subject from the fixation point to the reward target, and (E') identifying the subject as including a deficiency of the neurotransmitter if the non-reward saccade movement parameter (e.g., velocity) and the reward saccade movement parameter (e.g., velocity) are statistically equivalent.

In some embodiments of such a method, before the identifying step, there can be provided a step for determining a reward modulation of the subject that is equal to a difference between the reward saccade movement parameter (e.g., velocity) and a non-reward saccade movement parameter (e.g., velocity) (see, e.g., D in FIG. 21), wherein the identifying step includes determining whether the reward modulation of the subject is statistically equivalent to zero. Thus, instead of determining if the reward saccade movement parameter and non-reward saccade movement parameter are statistically equivalent, this step accomplishes a similar result by determining whether the reward modulation for the movement parameter is statistically significant. In either instances, such embodied methods do not necessarily require consideration of a reference saccade movement parameter and/or reference reward modulation for a particular movement parameter.

As described herein, the embodied methods can include the subject performing a reward saccade and a non-reward saccade have the same predetermined amplitude, including target amplitude. Embodied methods can also include diagnosing the subject with a neurodegenerative condition (e.g., Parkinson's disease) if the subject is determined to have a deficiency of the neurotransmitter (e.g., dopamine), and in some instances a treatment can be administered to a subject that is diagnosed with the neurodegenerative condition.

The presently-disclosed subject matter also includes a system for measuring a saccade in a subject. In some embodiments the components of a system can be similar to those known in the art. For exemplary systems and components thereof, see U.S. Patent Application Publication Nos. 2012/0081666, 2005/0099601, 2007/0177103, 2007/0132841, 2008/0049186, and 2008/0049187, which are all incorporated herein by reference. In some embodiments the system comprises a display for showing a fixation point, a reward target, and a non-reward target. The display can be one known in the art. For instance, in some embodiments the system is comprised of a virtual reality headset, a monitor, a screen, or the like. The visuals can be displayed on any suitable medium.

Embodiments of the present systems can also include a camera for tracking one or more saccade movement parameters of an eye between the fixation point and the target. The camera can be one that is known in the art that is capable of tracking the movement of an eye. The information collected from the camera can then be utilized to measure one or more saccade movement parameters. In some embodiments the camera includes an infrared eye sensor configured to track one or more movement parameters of the saccade. Exemplary cameras can track an eye by measuring the point of gaze (i.e., where the subject is looking) and/or the motion of an eye relative to the head. In some embodiments, in addition or instead of a camera, an eye tracker can be utilized that includes a contact mechanism that attaches to the eye of a subject and can measure eye movement. In other embodiments the eye tracker can include electrodes that can be placed near the eye of a subject to measure electrical potential generated for eye movement. In yet other embodiments direct observation can also be utilized.

Embodiments of the present systems can also include a processor that includes software for determining a reward modulations for one or more saccade movement parameters of the subject. In some embodiments the processor can also identify whether the reward modulation of the subject is statistically equivalent to zero. In some embodiments the processor can further identify whether there is a statistically measurable difference between the reward modulation of the subject and a reference reward modulation.

The processor provided in the system can carrying out one or more tasks. The processor can, for example, be capable of measuring saccade velocity, including peak saccade velocity, saccade amplitude, and/or saccade reaction time in response to a reward target and/or non-reward target. Certain processors can be capable of comparing differences in one or more saccade movement parameters to respective reference saccade movement parameters. Certain processors can be capable of comparing differences in reward modulation to a reference reward modulation. Still further, a processor can be capable of comparing one or more reward saccade movement parameters to respective non-reward saccade movement parameters.

In this regard, the terms "processor," "processing device," "computer," and "computing machine" are used interchangeably herein to describe one or more microprocessors, microcontrollers, central processing units, Digital Signal Processors (DSPs), Field-Programmable Gate Arrays (FPGAs), Application-Specific Integrated Circuits (ASICs), or the like, along with peripheral devices such as data storage device(s), input/output devices, or the like, for executing software instructions to perform substantial computations including numerous arithmetic operations or logic operations without human intervention during a run.

The present systems can further include a data storage device. The terms "data storage device," "computer memory," and "memory" are used interchangeably herein to mean physical devices (computer readable media) used to store programs (sequences of instructions) or data (e.g. program state information) on a non-transient basis for use in a computer or other digital electronic device, including primary memory used for the information in physical systems which are fast (i.e. RAM), and secondary memory, which are physical devices for program and data storage which are slow to access but offer higher memory capacity. Traditional secondary memory includes tape, magnetic disks and optical discs (CD-ROM and DVD-ROM). The term "memory" is often (but not always) associated with addressable semiconductor memory, i.e. integrated circuits consisting of silicon-based transistors, used for example as primary memory but also other purposes in computers and other digital electronic devices. Semiconductor memory includes both volatile and non-volatile memory. Examples of non-volatile memory include flash memory (sometimes used as secondary, sometimes primary computer memory) and ROM/PROM/EPROM/EEPROM memory. Examples of volatile memory include dynamic RAM memory, DRAM, and static RAM memory, SRAM. Data storage may also include remote (e.g., cloud) or other wireless storage systems.

In some embodiments the systems further comprise a holder configured to maintain a head of the subject in a stationary position. The holder can therefore help ensure that accurate saccadic measurements are taken without having to compensate for head movement of the subject. In specific embodiments the holder is a stationary bite bar that the subject can bite during a measurement procedure.

EXAMPLES

The presently-disclosed subject matter is further illustrated by the following specific but non-limiting examples. The following examples may include compilations of data that are representative of data gathered at various times during the course of development and experimentation related to the presently-disclosed subject matter.

Example 1

This Example describes procedures conducted to characterize the relationship between saccadic velocities and different factors. The factors that were varied included the initial start position (e.g., angle) of the eye, the amplitude of the saccade (e.g., degrees of eye movement), and the direction of the saccade (e.g., centrifugal (CF) or centripetal (CP). The procedures were also conducted both with and without visual reward, thereby characterizing the effects of rewards on saccadic movement, and particularly, the effects of certain neurons (e.g., dopamine neurons) on saccadic movement).

Two juvenile rhesus monkeys (*Macaca mulatta*, 4 and 7 kg) served as subjects. The general procedures for surgical implants, coil recording, animal training and anesthesia conformed to Guidelines for the Care and Use of Animals of National Institutes of Health. The animals were housed with ad lib food and water, and were attended to by full-time veterinarians. During the experiments, the animals' water intake was rescheduled based on operant conditioning procedures. The animals were surgically implanted with a head post over the skull and a search coil under the conjunctiva. During the experimental session, the animals were seated straight ahead in primate chairs. Horizontal and vertical eye positions were recorded within an electromagnetic field (M1; Riverbend, Inc.; M2: CNC Engineering, Inc.) at 500 Hz.

Visual targets were back-projected via an LCD projector onto a translucent screen. The screen was placed 72 cm in front of the animals, subtending ±50° horizontally and vertically. Visual target display, behavioral scheduling and data recording were controlled by an integrated data acquisition system (Beethoven; Ryklin, Inc.) that guaranteed a temporal resolution of 1 ms. A photoreceptor cell was placed at the screen corner to register the precise timing of target display.

Figure 1A:
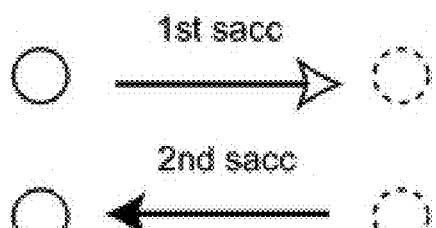
FIG. 1 includes (A) schematics and (B) position traces of two consecutive saccades from an initial fixation point to a visual target performed during a double-step saccade task, where the second saccade has a visual target corresponding the fixation point of the first saccade (H, horizontal eye position; V, vertical eye position; ▼, correction saccade).
Figure 1B:
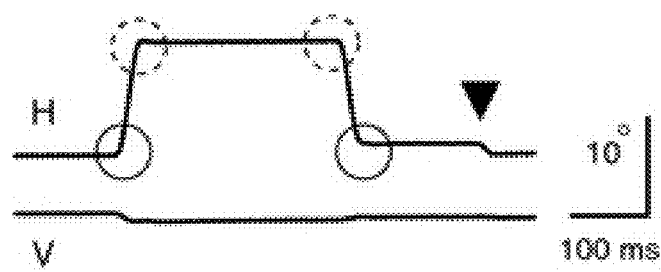

Animals were trained to make two consecutive visually-guided saccades (FIG. 1). The task started when the animal attained the first (green) target (subtending 1°; FIG. 1A, symbolized by an open circle). After fixation of 300-700 ms, the first target was extinguished and a second (red) target (subtending 1°; symbolized by a dashed circle) was displayed. The animal made a saccade to the second target (FIG. 1B; an upward deflection of the horizontal position trace). After the animal attained the second target it remained illuminated for an additional 50-300 ms. A third (green) target, displayed at the same location as the first target, was illuminated as soon as the second target was extinguished. The reward (a drop of juice) was given, contingent on the animal making a saccade to the third target (within a window of 3-8° radius; the downward deflection following the dashed circle in FIG. 1B) and then maintaining fixation for ≥300 ms. In the task, the first saccade (FIG. 1A; open rightward arrow) was never associated with a reward prospect, whereas the second saccade (FIG. 1A; filled leftward arrow) was. Both animals M1 and M2 were subjected to a reinforcement procedure with 80-100% reward rate on successful saccades. Animal M1 performed with 80-90% reward rate in ~70% of the data and 100% reward rate in the remaining data, whereas animal M2 performed with 100% reward rate in ~80% of the data and 90% reward rate in the remaining data. As the reward values did not vary significantly and there was little difference in the observed velocities, the velocity data were pooled and analyzed together. Only successful saccades are reported herein.

Initial target positions were primarily located along the horizontal and vertical meridians. A typical block of trials consisted of 9 to 12 randomly selected initial target positions (six to nine along the horizontal meridian and three along the vertical meridian), spaced at 2-6° intervals. For each initial target position there were eight possible horizontal target amplitudes, with amplitude intervals averaging 4° (e.g., ±4, ±8, ±12 and ±16° for one block, ±6, ±10, ±16 and ±20° for the other). These horizontal target amplitudes were intermixed with two or more vertical target amplitudes. A typical block of trials consisted of 54 to 72 randomly selected target-displacement-direction configurations.

Off-line analyses were performed using an in-house program on a Windows platform. General statistical analysis was performed using Statistica (StatSoft Co.). For the general linear model ANCOVA, homogeneity-of-slopes model was used to test slope difference, while ANCOVA was used to test intercept difference (StatSoft Co.; Tulsa, Okla.). Only horizontal saccades were included in the analysis. Data are presented as mean ±SD. Eye positions were smoothed using a five-point parabola filter. Saccade onset and offset were defined as when movement velocity exceeded or fell below a threshold of 30°/s. Movements were displayed on screen for visual inspection before measurement.

Over 25,000 horizontal saccades from each animal were included in the analysis. These horizontal saccades were visually inspected, such that saccades with >1.5° vertical amplitude component were excluded from further analysis. As evident in the vertical position trace shown in FIG. 1B, the horizontal saccade had a negligible vertical amplitude component (M1: leftward first saccade, −0.25±0.53°; rightward first saccade, −0.25±0.51°; leftward second saccade, −0.60±0.47°; and rightward second saccade, −0.62±0.42°; M2: leftward first saccade, 0.09±0.54°; rightward first saccade, −0.03±0.49°; leftward second saccade, −0.13±0.50°; and rightward second saccade, −0.26±0.45°). Based on the cumulative distribution of the onset latencies of visually guided saccades, the top and bottom 1% of the data were excluded from the subsequent analysis. As a result, the minimal onset latency cut-offs were 80 and 100 ms for animals M1 (149±36 ms) and M2 (135±17 ms), respectively. The same onset latency cutoffs were applied to the first and second saccades.

Example 2

Using the procedures set forth in Example 1, this Example characterizes the effects of different variables on saccadic velocities. Specifically, this Example characterizes saccadic peak velocities as a function of amplitude and reward prospect as well as the effects of initial eye position and reward prospect on saccadic velocity.

Saccadic Peak Velocity as a Function of Amplitude and Reward Prospect

Figure 2A:
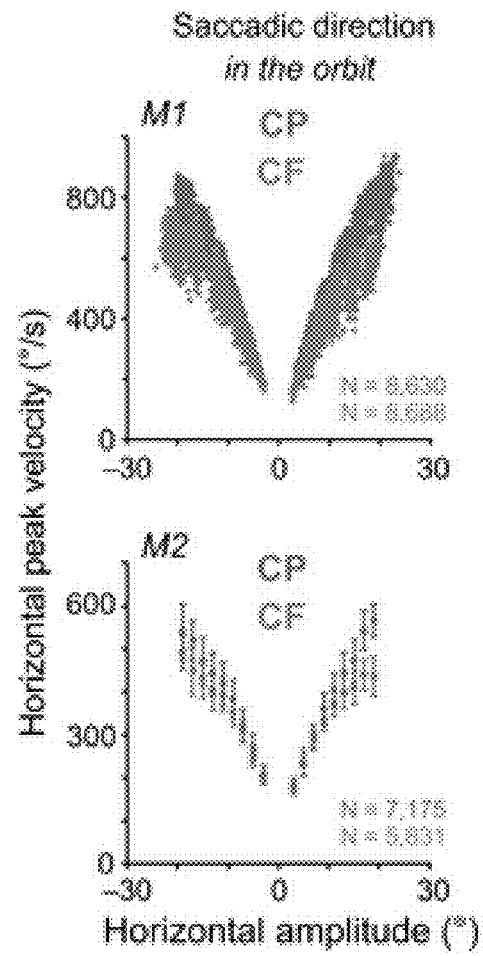
FIG. 2 includes graphs showing how (A) saccadic direction in the orbit and (B) the presence of reward prospect affected horizontal saccadic peak velocity as a function of horizontal saccadic amplitude (CP, centripetial; CF, centrifugal; R, saccade with reward visual stimulus; NR, saccade with non-reward visual stimulus).

Saccadic amplitude is known to be a critical predictor of saccadic peak velocity (FIG. 2). Horizontal saccades were selected that were unambiguously CP or CF for analysis. FIG. 2A shows that CP saccades were generally faster than CF saccades. This trend appeared to hold across amplitudes and animals, even though the difference appeared to diminish for saccades of smaller amplitudes. Nevertheless, saccadic direction in the orbit appeared to account for the differences in saccadic velocity, independently of variation in saccadic amplitudes.

Figure 2B:
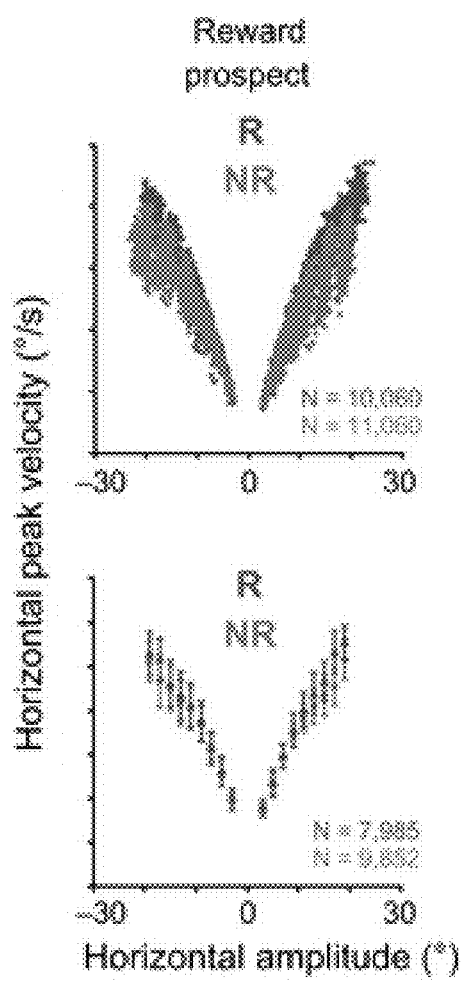

Saccades associated with reward prospect (R) and with no reward prospect (NR) were also selected. FIG. 2B shows that R saccades were generally faster than NR saccades. Again, this observation appeared to hold across amplitudes; that is, reward expectation accounted for the velocity variation, independently of saccadic amplitude. The findings were consistent for leftward and rightward saccades in both animals.

Figure 3A:
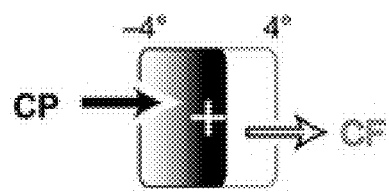
FIG. 3 includes (A) a schematic showing a rightward saccades wherein the white cross corresponds to the center of the orbit, the filled arrow corresponds to a CP saccade, and the open arrow corresponds to a CF saccade, and (B) a graph showing data from M1 plotted as a function of horizontal saccadic amplitude for centripetial (CP) and centrifugal (CF) saccades.
Figure 3B:
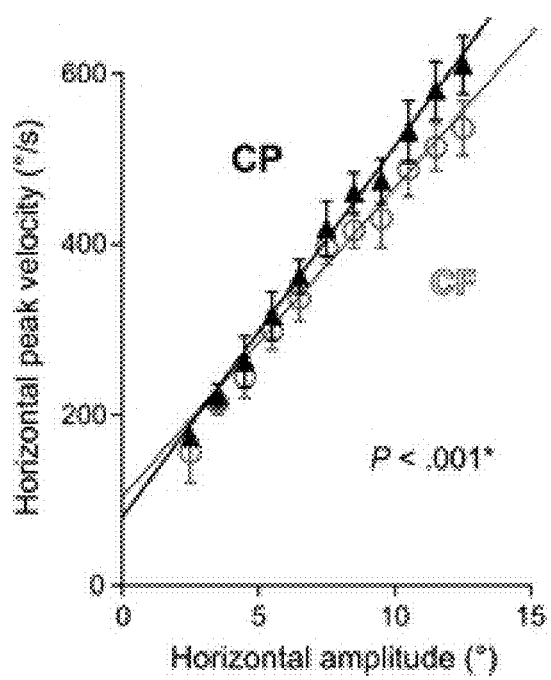

Based on FIG. 2, an ANCOVA was performed to assess the effect of saccadic direction while controlling saccadic amplitudes (Tables 1 and 2; FIG. 3). The data selected for analysis were separated into two groups based on initial eye positions. The first groups consisted of saccades with initial eye positions near the center of the orbit (±4°) and saccades with endpoints near the center of the orbit (Table 1). The second groups consisted of saccades with initial eye positions near an eccentric eye position (±5-16°) and saccades with endpoints near this eccentric eye position range (Table 2). FIG. 3 illustrates the ANCOVA for rightward saccades of M1. The CP and CF saccades selected had endpoints and initial positions, respectively, confined to a window within 4° from, but ≤1° over, the center of the orbit horizontally and ±4° from the orbital center vertically (FIG. 3; Table 1). The range of saccadic amplitudes tested was limited to a relatively linear range for each subject (M1, from 3 to 13°; and M2, from 3 to 11°). The ANCOVAS indicated that the slopes for CP saccades were significantly higher than those of CF saccades, for leftward and rightward movements (homogeneity-of-slopes test; P<0.001). That is, for given fixed saccadic amplitudes, CP saccades were faster than CF saccades, consistent with the results shown in FIG. 2A. All of the tests were significant (homogeneity-of-slopes test, P range 0.001-0.015), suggesting that saccadic direction in the orbit was an important predictor of saccadic velocity.

Table 2 shows the ANCOVA for saccades taking place at eccentric eye positions. The amplitude range of the saccades was identical to that in Table 1. Tables 1 and 2 are both shown below. The CP and CF saccades selected had endpoints and initial positions, respectively, confined to a window 5-16° from the center of the orbit horizontally and ±4° from the orbital center vertically. Again, the ANCOVA indicated that the slopes for CP saccades were significantly higher than those of CF saccades (homogeneity-of-slopes test; P<0.001 across the board). The results in Tables 1 and 2 together indicated that the velocity bias persisted even when the initial eye position was varied.

TABLE 1

Effect of saccadic direction in the orbit on saccadic peak velocity as a function of amplitude near the orbital center.

| | | Leftward saccade | | | | | Rightward saccade | | | | |
|---|---|---|---|---|---|---|---|---|---|---|---|
| | | Slope | r | n | F | P | Slope | r | n | F | P |
| M1 | CP | −43.8 | −0.97 | 896 | 162.6 | 0.000* | 43.5 | 0.97 | 826 | 228.3 | 0.000* |
| | CF | −37.8 | −0.96 | 990 | | | 36.3 | 0.96 | 1095 | | |
| M2 | CP | −29.1 | −0.88 | 704 | 5.9 | 0.015* | 30.6 | 0.96 | 693 | 11.7 | 0.001* |
| | CF | −26.8 | −0.82 | 668 | | | 29.0 | 0.96 | 661 | | |

CP saccades had end points confined to a window within 4° from, but ≤1° over, the centre of the orbit horizontally and ±4° from the orbital centre vertically. CF saccades had initial positions confined to a window within 4° from, but ≤1° over, the centre of the orbit horizontally and ±4° from the orbital centre vertically. The amplitude range of horizontal saccades included for the regression analysis was 3-13° for M1 and 3-11° for M2. Slope, the main sequence relationship between peak velocity and saccadic amplitude (see main text for details); r, Pearson correlation coefficient; F-value, homogeneity-of-slopes test;
*P < 0.05.

TABLE 2

Effect of saccadic direction in the orbit on saccadic peak velocity as a function of amplitude at eccentric eye positions.

| | | Leftward saccade | | | | | Rightward saccade | | | | |
|---|---|---|---|---|---|---|---|---|---|---|---|
| | | Slope | r | n | F | P | Slope | r | n | F | P |
| M1 | CP | −47.0 | −0.97 | 629 | 548.0 | 0.000* | 45.6 | 0.98 | 619 | 681.7 | 0.000* |
| | CF | −32.4 | −0.95 | 656 | | | 31.1 | 0.94 | 788 | | |
| M2 | CP | −31.2 | −0.89 | 962 | 130.5 | 0.000* | 31.7 | 0.95 | 1085 | 291.6 | 0.000* |
| | CF | −24.2 | −0.89 | 1168 | | | 24.4 | 0.95 | 1026 | | |

CP saccades were directed toward a window 5-16° from the centre of the orbit horizontally and ±4° from the orbital centre vertically. CF saccades were directed away from a window 5-16° from the centre of the orbit horizontally and ±4° from the orbital centre vertically. The amplitude range of horizontal saccades for each subject is the same as in Table 1;
*P < 0.01.

Figure 4A:
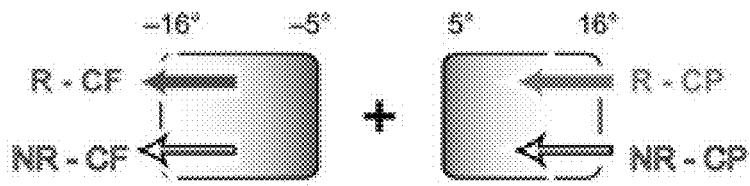
FIG. 4 includes (A) a schematic showing different leftward saccades, and (B, C) graphs showing data plotted as a function of horizontal saccadic amplitudes for CP saccades associated separated reward prospect (R-CP), CF saccades associated with reward prospect (R-CF), CP saccades associated with no reward prospect (NR-CP), and CF saccades associated with no reward prospect (NR-CF).
Figure 4B:
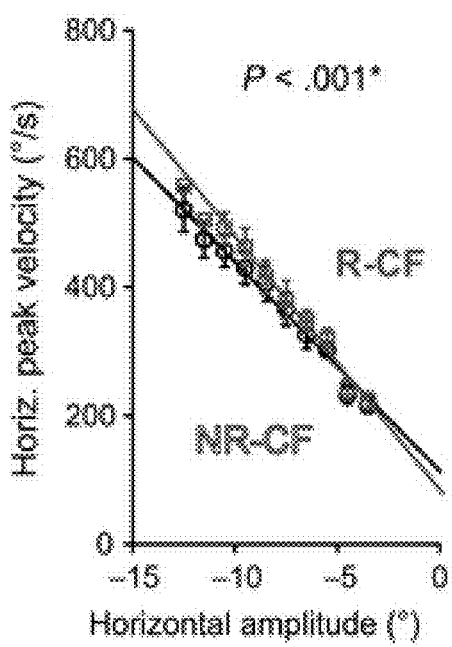
Figure 4C:
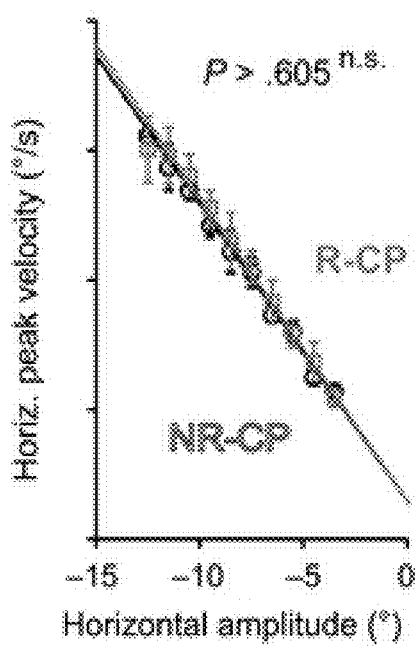

ANCOVA was performed for the saccades associated with the prospect of reward and the ones without (Tables 3 and 4; FIG. 4). The selection of saccadic amplitude range and the test range of eye positions was identical to that reported in Tables 1 and 2 except that the saccades were grouped under four categories: CF saccades with reward prospect (R-CF), CF saccades with no reward prospect (NR-CF), CP saccades with reward prospect (R-CP) and CP saccades with no reward prospect (NR-CP; FIG. 4A). FIG. 4 illustrates an example of the pairwise comparison between R-CF and NR-CF saccades (FIG. 4B) and between R-CP and NR-CP saccades (FIG. 4C). The graph shows that R-CF saccades had a higher negative slope than NR-CF saccades, for leftward and rightward movements (homogeneity-of-slopes test; P<0.001). The slope difference between R-CP and NR-CP saccades was not significant (P>0.605).

Tables 3 and 4, both shown below, summarize the results of the ANCOVA for the effect of reward prospect. For given fixed saccadic amplitudes, R-CF saccades had significantly higher slopes than NR-CF saccades (homogeneity-of-slopes test; P<0.01). This trend appeared to hold whether the saccades were (i) toward or away from the center of the orbit (Table 3) or (ii) at an eye position range deviating from the orbital center (Table 4). This observation was consistent for rightward and leftward saccades in both subjects. The difference in slopes between R-CP and NR-CP saccades was not significant (Tables 3 and 4), consistent with the results in FIG. 4C. Again, this observation appeared to hold for rightward and leftward saccades in both animals.

TABLE 3

Effect of reward expectation on saccadic peak velocity as a function of amplitude near the orbital center.

| | | Leftward saccade | | | | | Rightward saccade | | | | |
|---|---|---|---|---|---|---|---|---|---|---|---|
| | | Slope | r | n | F | P | Slope | r | n | F | P |
| M1 | R-CP | −44.3 | −0.98 | 607 | 3.6 | 0.057 | 43.7 | 0.97 | 537 | 1.1 | 0.302 |
| | NR-CP | −42.9 | −0.98 | 289 | | | 42.9 | 0.98 | 289 | | |
| | R-CF | −40.7 | −0.97 | 221 | 18.9 | 0.000* | 39.1 | 0.97 | 251 | 27.3 | 0.000* |
| | NR-CF | −37.1 | −0.97 | 769 | | | 35.4 | 0.96 | 844 | | |

TABLE 3-continued

Effect of reward expectation on saccadic peak velocity as a function of amplitude near the orbital center.

| | | Leftward saccade | | | | | Rightward saccade | | | | |
|---|---|---|---|---|---|---|---|---|---|---|---|
| | | Slope | r | n | F | P | Slope | r | n | F | P |
| M2 | R-CP | −27.6 | −0.80 | 295 | 0.0 | 0.859 | 31.0 | 0.96 | 296 | 2.0 | 0.162 |
| | NR-CP | −27.8 | −0.86 | 409 | | | 30.1 | 0.97 | 397 | | |
| | R-CF | −30.8 | −0.89 | 306 | 5.5 | 0.002* | 29.9 | 0.96 | 298 | 6.9 | 0.008* |
| | NR-CF | −27.0 | −0.76 | 362 | | | 28.2 | 0.96 | 363 | | |

Data include CP saccades with reward prospect (R-CP), CP saccades associated with no reward prospect (NR-CP), CF saccades with reward prospect (R-CF) and CF saccades associated with no reward prospect (NR-CF). The amplitude range and saccadic starting and end points of horizontal saccades for each subject are the same in Table 1;
*$P < 0.01$.

TABLE 4

Effect of reward expectation on saccadic peak velocity as a function of amplitude at eccentric eye positions.

| | | Leftward saccade | | | | | Rightward saccade | | | | |
|---|---|---|---|---|---|---|---|---|---|---|---|
| | | Slope | r | n | F | P | Slope | r | n | F | P |
| M1 | R-CP | −46.5 | −0.96 | 477 | 0.3 | 0.606 | 45.3 | 0.97 | 447 | 0.9 | 0.345 |
| | NR-CP | −45.8 | −0.99 | 152 | | | 46.4 | 0.98 | 172 | | |
| | R-CF | −39.7 | −0.97 | 132 | 34.1 | 0.000* | 36.1 | 0.96 | 147 | 22.2 | 0.000* |
| | NR-CF | −32.5 | −0.95 | 524 | | | 30.7 | 0.93 | 641 | | |
| M2 | R-CP | −31.4 | −0.88 | 883 | 2.2 | 0.135 | 31.7 | 0.94 | 934 | 2.8 | 0.093 |
| | NR-CP | −35.1 | −0.95 | 79 | | | 33.7 | 0.97 | 151 | | |
| | R-CF | −28.0 | −0.92 | 123 | 7.5 | 0.006* | 29.2 | 0.95 | 59 | 11.0 | 0.001* |
| | NR-CF | −23.7 | −0.88 | 1045 | | | 24.3 | 0.94 | 967 | | |

The amplitude range and saccadic starting and end points of horizontal saccades for each subject are the same as in Table 3. Format same as in Table 1;
*$P < 0.01$.

Without being bound by theory or mechanism, there is a possibility that target predictability, in addition to reward prospect, facilitated saccadic velocities in the double-step saccade task. This issue is raised because the second, rewarded, saccade in the task was always made to the third target in the direction opposite to the first saccade. In contrast, in a typical single-step saccade task, saccadic direction might vary such that the direction (and timing) of the rewarded saccade could not be predicted based on that of the preceding saccade. Based on this reasoning, the rewarded target of single-step saccades was not considered for the purposes of this Example to be predictable, whereas that of double-step saccades was.

Figure 5A:
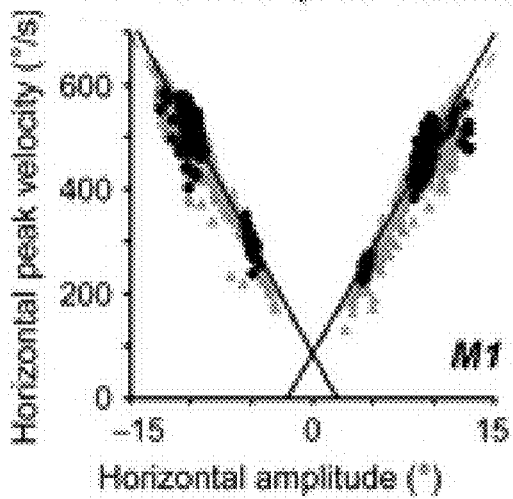
FIG. 5 includes graphs for subjects (A) M1 and (B) M2 showing the horizontal saccadic peak velocities as a function of horizontal amplitude for single-step (●) and double-step (∆) R-CF saccade tasks with initial eye positions near the center of the orbit.
Figure 5B:
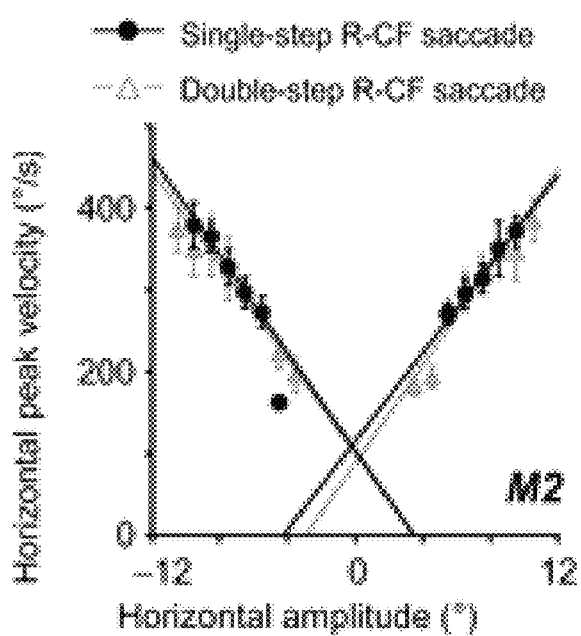

Consequently, R-CF saccades were compared between the double-step and single-step saccade tasks in which initial eye positions were near the orbital centers. FIG. 5 plots the main sequence relationship between saccadic peak velocity and saccadic amplitude, showing little difference in the peak saccadic velocities between the two tasks. The ANCOVA confirmed that the slopes of the two tasks were not significantly different from each other (homogeneity-of-slopes test; P>0.05 across the board), indicating that target predictability accounted little for the observed main sequence relationship between velocity and amplitude. Instead, the presence of reward prospect was a factor that sustained the level of the observed saccadic peak velocities.

In sum, in addition to saccadic amplitude, initial eye position with respect to saccadic direction and reward expectation can be predictors of saccadic peak velocity. Nevertheless, for some saccades less than or equal to 5° saccadic velocity was not significantly modulated by saccadic direction or reward expectation.

Effect of Initial Eye Position on Saccadic Peak Velocity

Figure 6:
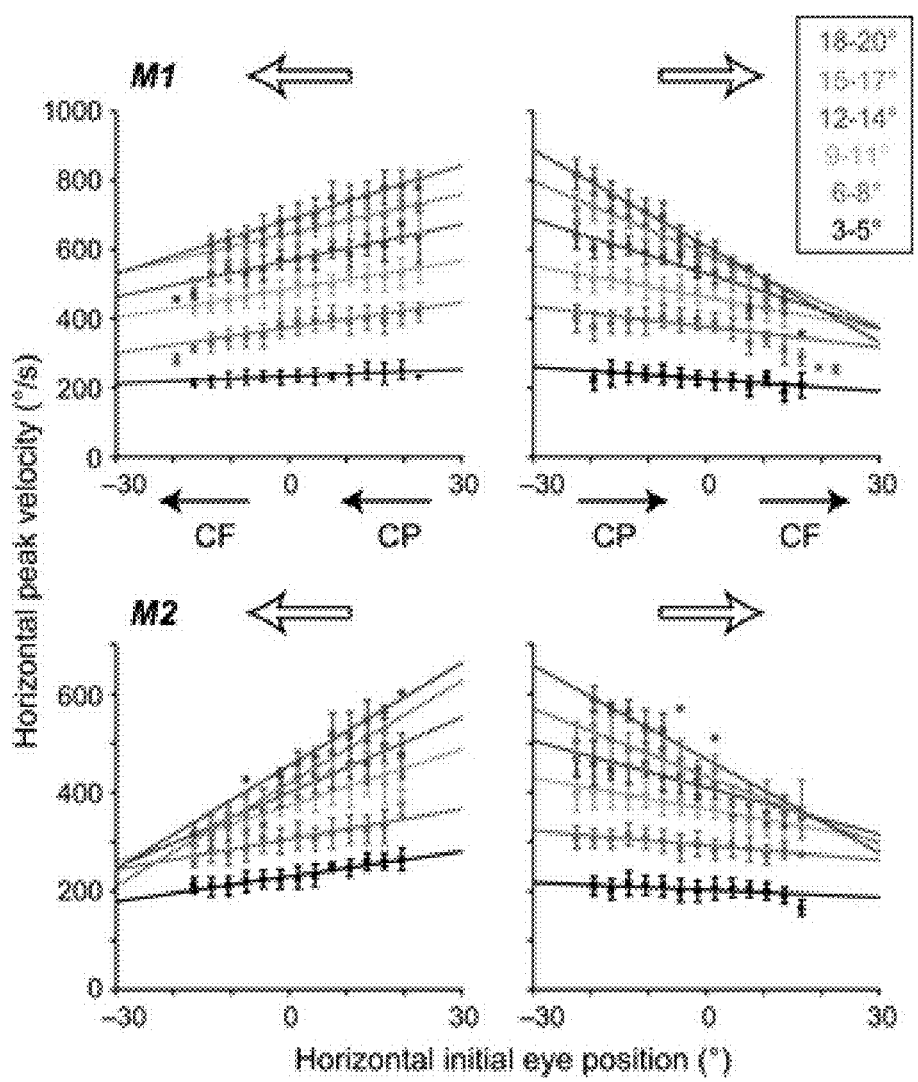
FIG. 6 includes graphs showing saccadic peak velocity as a function of horizontal initial eye position for CF and CP movement and with different amplitudes for the M1 and M2 subjects.
Figure 7A:
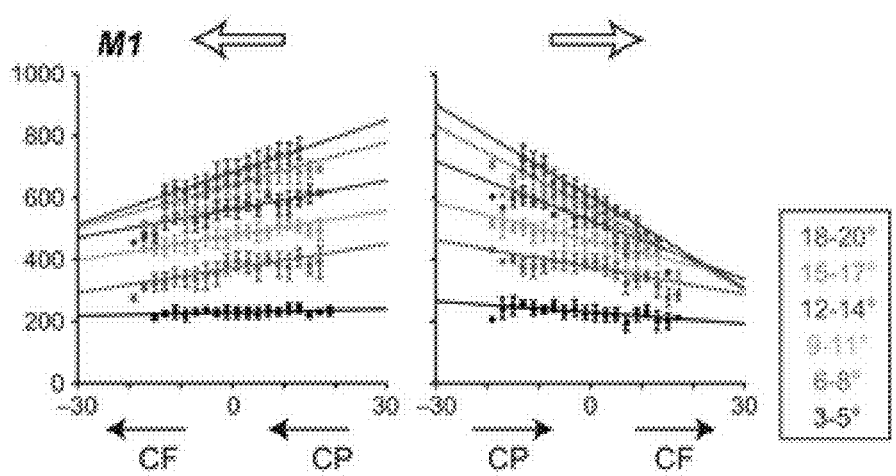
FIG. 7 includes graphs showing saccadic peak velocity as a function of horizontal initial eye position for CF and CP movement and with different amplitudes for the M1 and M2 subjects when using (A,C) a non-reward visual stimulus and (B,D) a reward visual stimulus.
Figure 7B:
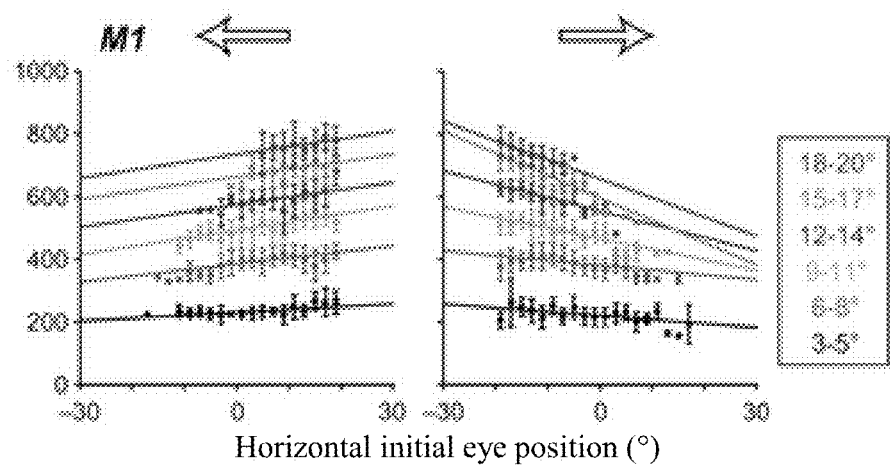
Figure 7C:
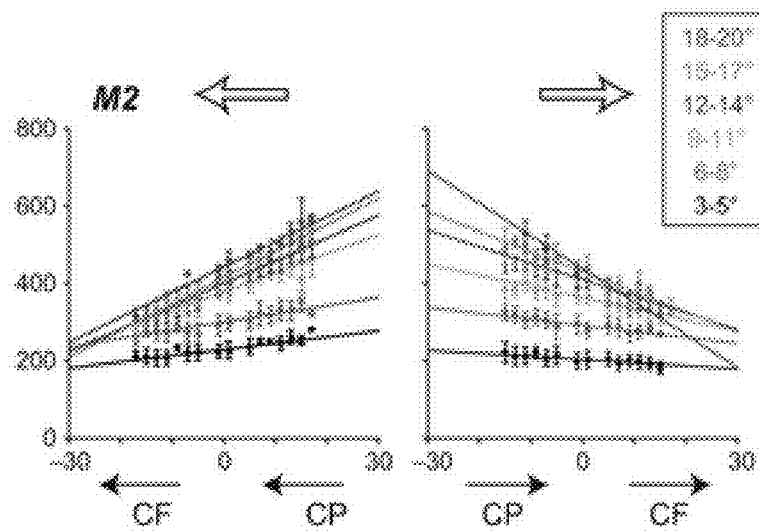
Figure 7D:
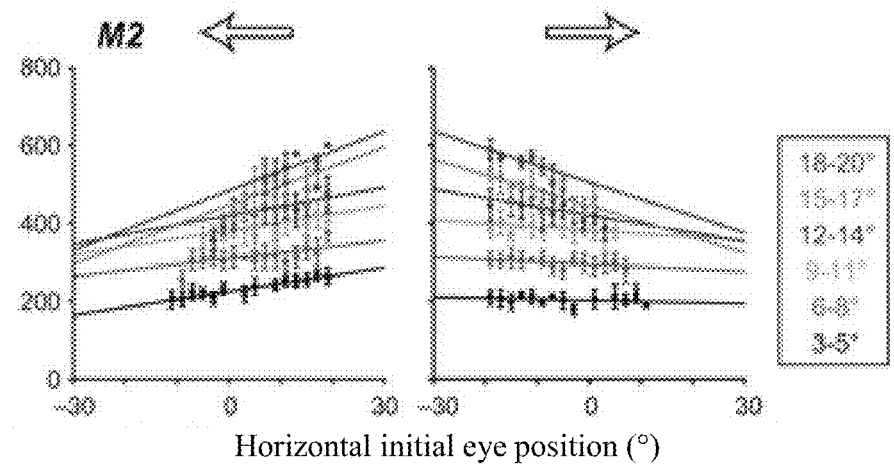

The data were separated for different amplitude ranges (3-5, 6-8, 9-11, 12-14, 15-17 and 18-20°) and for saccadic directions in space (leftward, <=; rightward, =>). Initial eye position was limited to ±20° from the orbital center. For each amplitude range, saccadic peak velocity decreased linearly as horizontal initial eye position deviated in the direction of the saccade. This bias existed across all amplitudes (Pearson correlation, P<0.01), even though the slopes of ≤5° saccades were close to zero. In addition, the slopes increased as amplitudes increased. This trend was found in leftward and rightward saccades of both animals, consistent with our prior observation (FIG. 3; Tables 1 and 2). The velocity range increased as saccadic amplitudes increased (FIG. 6). This observation was consistent with the variability of saccadic velocity observed in the so-called main sequence relationship (FIG. 2).

Effect of Reward Prospect on the Saccadic Velocity Bias

FIG. 7 separates the data of FIG. 6 into two groups: saccades without (A and C) and with (B and D) the prospect of reward. Only the data with initial eye positions within ±20° (functional oculomotor range for nonhuman primates) were considered in this analysis. The saccadic velocity bias existed in the absence of reward prospect. Saccadic peak velocity decreased linearly as the initial eye position deviated in the direction of the saccade, and the slope increased as amplitudes increased (M1, A; M2, C). However, in the presence of reward prospect the slopes decreased (M1, B; M2, D), suggesting that reward expectation modulated saccadic velocity away from the orbit includes more velocity than saccades toward the center of the orbit, consistent with our prior analysis (FIG. 4). That is, the reward gain modulation over saccadic velocity was not uniform across initial eye positions.

Figure 8A:
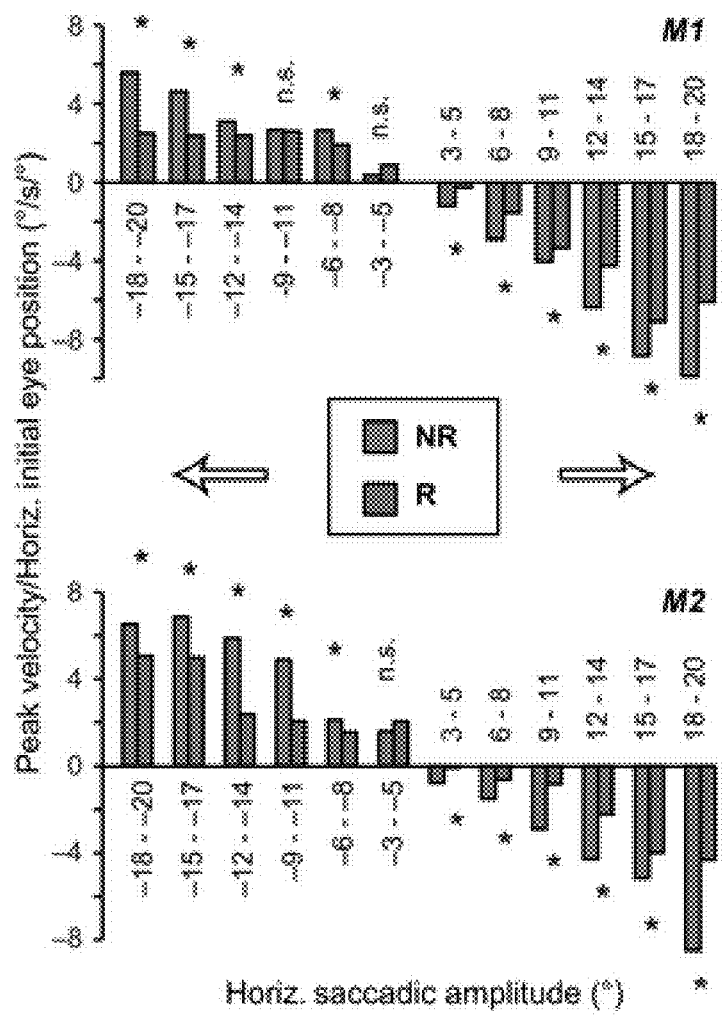
FIG. 8 includes graphs showing (A) the slopes calculated from FIG. 7 for saccades associated with reward visual stimulus (R), saccades with non-reward visual stimulus (NR), and subjects M1 and M2, (B) the slope of NR saccades plotted as a function of horizontal saccadic amplitude, and (C) the slope difference between R and NR saccades plotted as a function of horizontal saccadic amplitude.
Figure 8B:
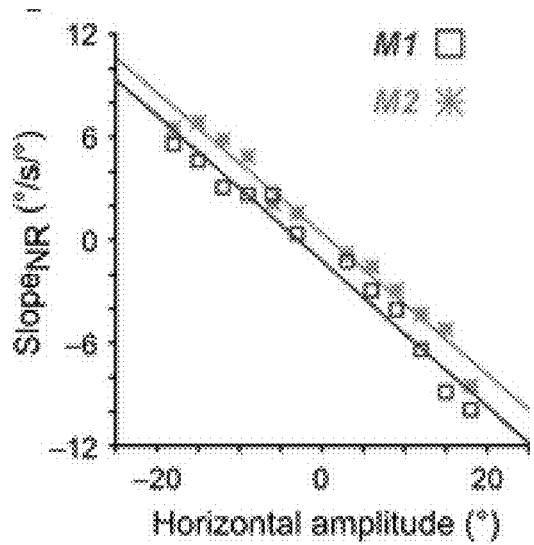
Figure 8C:
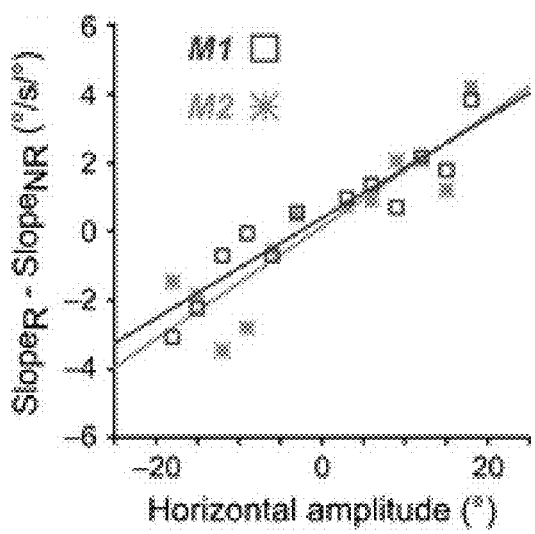

FIG. 8A also shows that reward expectation (for R saccades) significantly reduced the slopes across nearly all amplitudes (homogeneity-of-slopes test; P<0.01). FIG. 8C quantified the effect of reward expectation by plotting the residual of reward modulation as the slope difference between R and NR saccades. This reward modulated velocity bias (in the orbit) was a linear function of saccadic amplitudes with a slope ranging from 0.15 to 0.16 (P <0.01; FIG. 8C), similar to the amplitude-modulated velocity bias in the absence of reward prospect, which presumably resulted from a biomechanical regulation (FIG. 8B).

Figure 9A:
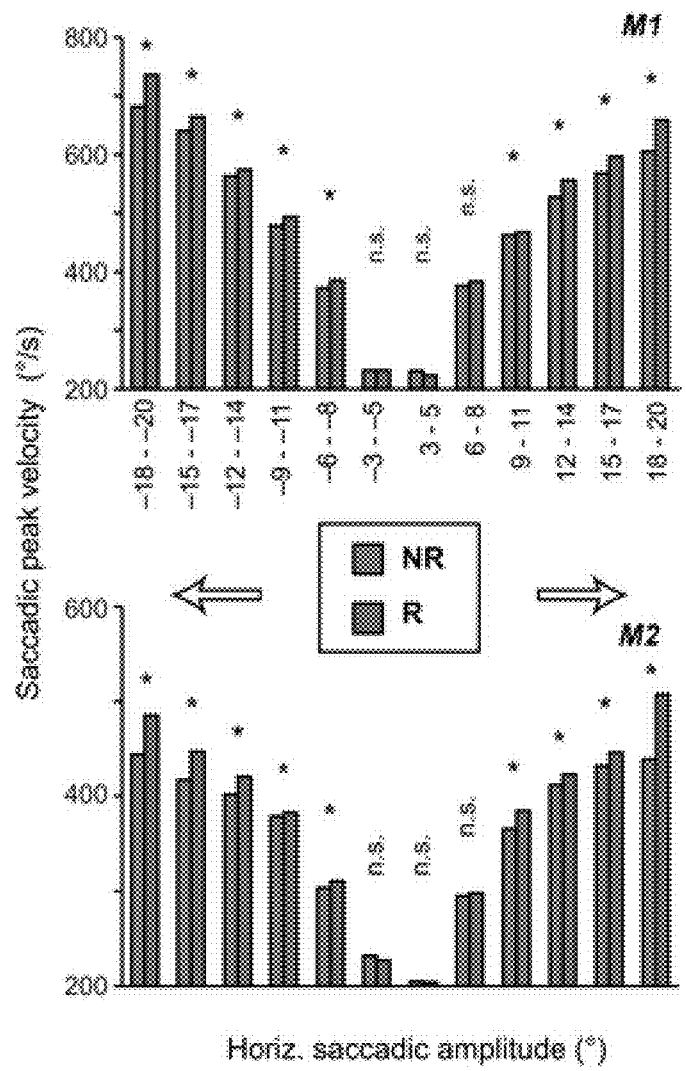
FIG. 9 includes graphs showing (A) the intercepts from FIG. 7 for saccades associated with reward visual stimulus (R), saccades with non-reward visual stimulus (NR), and subjects M1 and M2, (B) the intercept of NR saccades plotted as a function of horizontal saccadic amplitude, and (C) the intercept difference between R and NR saccades plotted as a function of horizontal saccadic amplitude.
Figure 9B:
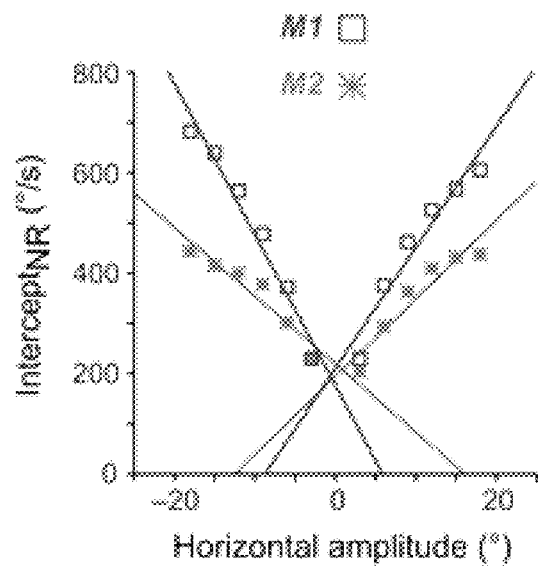

FIG. 9A quantifies the magnitude (intercept) of this bias as a function of amplitudes in the absence of reward prospect. Intercept reflects the peak velocity when the initial eye position had a zero value, i.e. when the initial eye position was centered in the orbit. In essence, this measure quantifies the main sequence relationship between saccadic peak velocity and amplitude when the eye is centered in the orbit. There existed a positive correlation between saccadic peak velocity and saccadic amplitude (FIG. 9B).

Figure 9C:
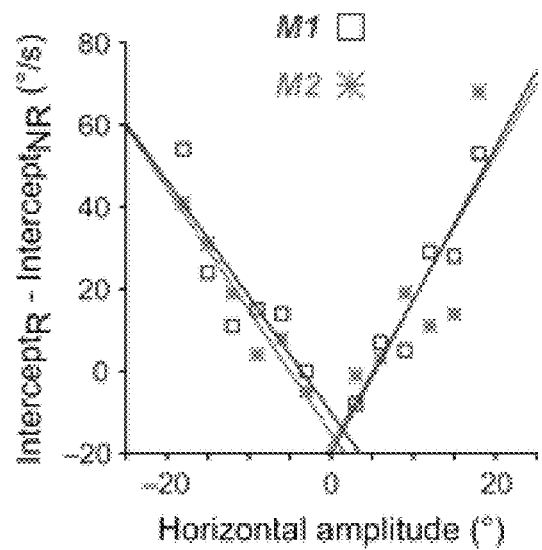

FIG. 9A also shows that reward expectation increased the intercepts of R saccades, compared to those of NR saccades, across nearly all amplitudes (ANOVA; P<0.01). There was no significant difference for smaller amplitude saccades (−3 to −5°, 3-5 and 6-8° for both M1 and M2; FIG. 9A). FIG. 9C quantifies the effect of reward expectation by plotting the magnitude of reward modulation as the intercept difference between R and NR saccades. The differences were linearly correlated with saccadic amplitudes (P<0.01; FIG. 9C). The slopes of this magnitude modulation were within a close range (leftward saccades, −2.82 for M1 and −2.99 for M2; rightward saccades, 3.73 for M1 and 3.72 for M2), despite differences in saccadic directions and animal differences (M2 being slower than M1). This magnitude modulation by reward prospect was consistent with that observed for NR saccades.

Additional tests were performed selecting saccades with similar (>50%) CP components for comparison (data not shown). Both rewarded and unrewarded saccades had a similar range of initial eye positions. The differences in slopes and intercepts between R and NR saccades persisted in a manner similar to the results of FIGS. 7 to 9.

Accordingly, the data suggest the existence of a saccadic velocity bias in the orbit, wherein saccadic velocity decreases linearly as the initial eye position deviated in the direction of the saccade (FIGS. 6 to 8). Second, it appeared that the slope of the velocity bias increased linearly as saccadic amplitude increased (FIG. 8B). That is, the velocity range increased as saccadic amplitude increased (FIG. 6), resulting in velocity variability in the so-called main sequence correlation with saccadic amplitude (FIG. 2). Third, reward expectation appeared to be a variable modulating saccadic velocity (FIG. 2), although reward gain modulation over saccadic velocities was not uniform across initial eye positions (FIGS. 7 and 8). The rate (slope) and magnitude (intercept) of reward modulation over the velocity bias in the orbit were linearly correlated with saccadic amplitudes (FIGS. 8C and 9C), independent of saccadic directions (in space) and animal differences. Smaller (≤5°) saccades received little reward modulation regardless of changes in initial eye positions.

Example 3

This Example describes a procedure, similar to the procedures described in the previous Examples, that were performed on human subjects. The procedures were intended to characterize the relationship between rewards and saccadic movements in the human subjects.

Subjects

Seven healthy subjects (4 female and 3 male, aged 18-52 years old) participated in this study. All subjects had normal or corrected-to-normal vision with no known neurological and psychiatric disorders. All subjects received verbal/written instructions.

Recording of Gaze Positions

Horizontal eye positions were recorded from subjects' right eye using a Skalar IRIS infrared limbus tracker (Delft, Netherlands; spatial resolution: 0.1°) (Reulen et al., 1988) at 500 Hz. Subjects were seated 52-cm in front of a computer monitor (27", resolution: 1080×800 pixels, 96 DPI, refresh rate: 75 Hz). Subjects' head position and orientation were restricted by the combination of a chin rest and a bite-bar. The height of the chin rest was adjusted, such that the subjects' eyes were leveled with the center of the monitor. The right eye of the binocularly viewing subject's was centered with the screen. Visual stimulus display, behavioral scheduling, and data recording were controlled by a real-time data acquisition system (Beethoven; Ryklin, Inc., New York), which guaranteed a temporal resolution of 1 ms.

Behavioral Procedures

Prior to each recording, subjects were told about the conditional stimulus-response procedure. Subjects were told that they would be paid for making a correct saccade in response to a congruent conditional stimulus (money bag) and they would not be paid for making a correct saccade in response to an incongruent stimulus (empty bag). Each subject was given 5-10 trials to practice before the recording began.

Each trial started with a white plus sign (1.2°) displayed on the center of a gray screen (RGB: 60/60/60). As soon as the subject fixated at the plus sign, a green arrow (RGB: 0/155/0, dimension:)1.7°) was displaced at the fixation location for 600 ms. The arrow served as the instruction signaling the target direction (left versus right) associated with monetary reward. The arrow was then replaced by a fixation dot (red, RGB: 255/0/80, 1.2° in diameter) for 600 -700 ms. Then, a "beep" tone signaled that a saccade test was to follow.

The test stimuli consisted of a conditional stimulus (i.e., a green money bag or a white empty bag), displayed at the fixation position, and 2 choice targets, placed symmetrically and horizontally from the conditional stimulus. The subjects' job was to review the conditional stimulus and to make a saccade to one of the choice targets within 1,500 ms. The conditional stimuli were either a congruent stimulus (a green money bag, dimension: 1.7°) or an incongruent stimulus (a white empty bag, dimension: 1.7°). The choice targets were blue dots (RGB: 0/175/240, 1.2° in diameter), placed 6° -11° eccentric from the conditional stimulus (For subject F1, the targets were displayed at ±6°, ±7°, ±8°, ±9°, ±10°, and ±11°; for other subjects, ±6°, ±7°, ±8°, ±9°, and ±10°). The correct choice target for the congruent stimulus was in the same direction as the instruction arrow, whereas that for the incongruent stimulus was opposite from the instruction arrow. The test stimulus stayed illuminated until the subject made a saccade or the maximum response time (1,500 ms) expired. Subjects were told to make just one saccade. There was no time pressure for the subjects to respond quickly. Target fixation was imposed for the initial 80-ms out of the entire 200 ms duration of target display. This was implemented so that eye blinking following fixation would not abort the trial. Follow the same reasoning, the (red) central fixation was imposed for the initial 200-ms out of the entire duration (600-700 ms). The fixation "window" was ±4° from the designated coordinate.

Each trial consisted of up to 3 series of saccade tests. Each saccade test repeated the steps of fixate, review instruction, fixate, review conditional stimulus, and make a choice. There were three trial types, randomly interleaved in the same block. The first trial type consisted of a single saccade test: a money bag. The second trial type consisted of 2 series of saccade tests that included an empty bag followed by a money bag. The third trial type consisted of 3 series of saccade tests that included an empty bag, followed by an empty bag, and followed by a money bag. The arrow directions, trial types, and target eccentricities were randomly selected for each trial in order to minimize subjects' anticipation and adaptation. Given a flawless task performance, the overall reward rate was pre-determined: 33%, 50%, and 100% for the first, second, and third saccade test, respectively. However, based on the post-hoc subject interview, none of the subjects was aware of the difference in the reward probability between the first and second saccade tests.

Sound feedback was provided during the task. After the subject made a correct saccade in response to the congruent stimulus, the sound of coin drop in a cash register was played. This signaled that a coin (i.e., 10¢) was deposited to the subject's bank. No sound was played after a correct saccade was made based on the incongruent stimulus, and no coin was deposited. To discourage making errors, the subjects were penalized for making an incorrect saccade in response to either a congruent or an incongruent stimulus. In this case, Homer Simpson's "Do'h" voice was played and a coin was removed from the subject's bank (i.e., −10¢). The errors varied from subject to subject, typically comprised about 1-5% of the data. Aborted trials, including failure to fixate (e.g., excessive blinking) or failure to respond before the maximum response time expired, were not penalized.

Each trial lasted 2.5 to 4.0 seconds, and the inter-trial interval was set at 1.2 seconds. The subjects were given approximately 30 seconds of break time after completing each block of 100 successful rewarded saccades. They were told to close their eyes and relax without removing themselves from the chin rest. A recording session typically lasted 30 minutes, and lasted a maximum of one hour.

Data Analyses

Off-line analyses were performed using a proprietary software program. Eye positions were smoothed using a 5-point parabola filter (Chen et al., 2013, Chen and Walton, 2005). Saccade onset and offset were defined when movement velocity exceeded or fell below a threshold of 30°/s. Movements were displayed on screen for visual inspection before measurement. Eye movements with double peaks in velocity profiles (<1% of data), likely resulting from eyelash artifacts or blinking, were removed from further analysis.

Only successful trials in which all saccades within the trials were correctly performed were included in the present study. Usually, the subject's performance improved rapidly in a few trials. The present analyses included only the correct trials after the subject's performance reached a considerably stable level, i.e., 5 consecutive successful trials. In addition, the first 3 trials immediately following each break were excluded from the analysis.

Since saccadic velocity has been shown to be coupled with amplitudes, saccadic velocities based on assorted amplitude bins were quantified (Bahill et al., 1975, Chen et al., 2013). The saccadic velocity of a given amplitude bin was initially assigned as the averaged velocity value of the bin. To guard against the estimate irregularity resulting from data binning, the velocity estimate was then averaged with those of two adjacent (forward and backward) bins. This 3-point moving average was applied once to the velocity-amplitude series under the same experimental treatment, prior to further analyses.

The percent change of peak velocity (% $C_{PV}$) across amplitude bins was quantified as:

$$\% \, C_{PV} = \left( \sum_i^n \frac{PV_{Ai} - PV_{Bi}}{PV_{Ri}} \right) \Big/ n \quad (1)$$

where $PV_{Ai}$ is the average peak velocity (PV) at bin i for saccade A, while $PV_{Bi}$ is the average PV at bin i for saccade B. For example, for the computation of reward modulation, saccade A is rewarded (R) saccade (i.e., $PV_{Ai}=PV_{Ri}$), whereas saccade B is unrewarded (UR) saccade (i.e., $PV_{Bi}=PV_{URi}$). Each bin width is 0.5°. n is the total number of amplitude bins, each of which consists of valid measures obtained from saccades A and B.

The change of saccadic PV ($C_{PV}$) across amplitude bins was quantified as:

$$C_{PV} = \frac{\sum_i^n (PV_{Ai} - PV_{Bi})}{n} \quad (2)$$

where $PV_{Ai}$ is the average PV at bin i for saccade A, while $PV_{Bi}$ is the average PV at bin i for saccade B. For example, for the computation of the nasal-temporal velocity asymmetry, saccade A is the saccade of the temporal (T) direction (i.e., $PV_{Ai}=PV_{Ti}$), whereas saccade B is the saccade of the nasal (N) direction (i.e., $PV_{Bi}=PV_{Ni}$). Each bin width is 0.5°. n is the total number of amplitude bins, each bin of which consists of valid measures of saccades A and B.

Statistical analysis was performed using Statistica (StatSoft Co., Tulsa, Okla.; Snedecor and Cochran, 1989). Data were described as mean ±S.E.M. unless otherwise specified.

Example 4

Using the procedures set forth in Example 3, this Example characterizes the effects of different variables on saccadic velocities.

Figure 10:
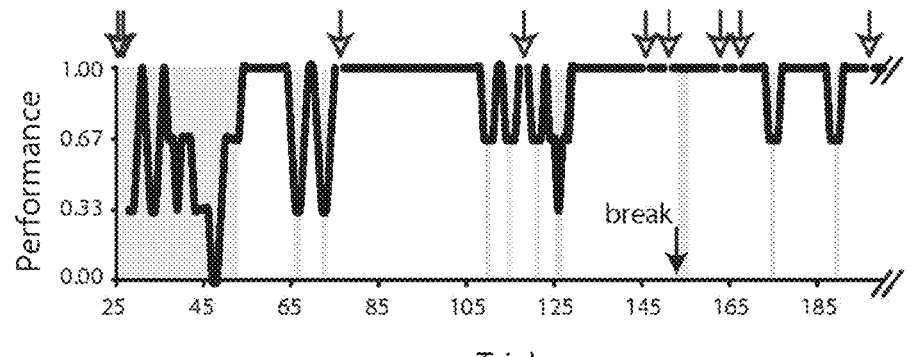
FIG. 10 includes a graph showing task performance of a conditional saccade from subject F3, wherein open arrows indicate the aborted trials, the filled arrow indicates one of the breaks during the recording session, and wherein the trials in the gray patches include the beginning trials (trials 28-53), 3 trials immediately after a break (trials 154-156), and all error trials.

The analyses were conducted on about 6.0° to about 10.5° horizontal saccades obtained from 7 (4 female and 3 male) subjects. Only the saccades of successful trials were included in the present analysis. FIG. 10 plots a typical task performance of the conditional saccades. A trial was considered successful if all of the series of saccadic choices were correct. A successful trial was counted as 1, whereas an unsuccessful one was counted as 0. The performance was illustrated as 3-point moving averages of the success scores. It was typical that the subject's performance improved rapidly after a brief period of practices. As the performance stabilized, i.e., reaching the level of 5 consecutive successes, the saccades of successful trials were selected for further analyses. The success rate was 91%, 80%, 71%, 80%, 77%, 85% and 84% for subject F1, F2, F3, F4, M5, M6 and M7, respectively.

Reward Modulation on the Saccadic Amplitude-Velocity Relationship

Figure 11A:
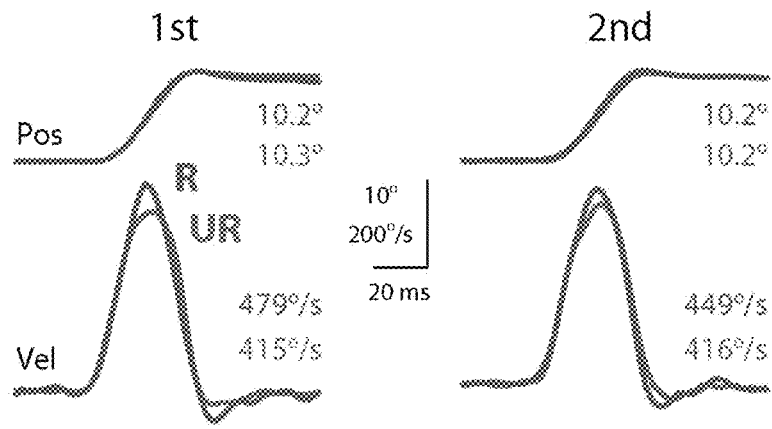
FIG. 11 includes graphs of data from subject F1 for first, left and second, left tests showing (A) exemplar position (top) and velocity (bottom) traces, and (B) the amplitude-velocity main sequence relationship between rewarded and unrewarded saccades, where the amplitudes (abscissa) of rightward and leftward saccades were assigned positive and negative values, respectively.

FIG. 11A showed exemplar position (top) and velocity (bottom) traces of rightward saccades. It can be noted that these saccades had comparable amplitudes (10.2°-10.3°). Rewarded saccades (first test: 479°/s; second test: 449°/s) were faster than unrewarded saccades (first test: 415°/s; second test: 416°/s).

Figure 11B:
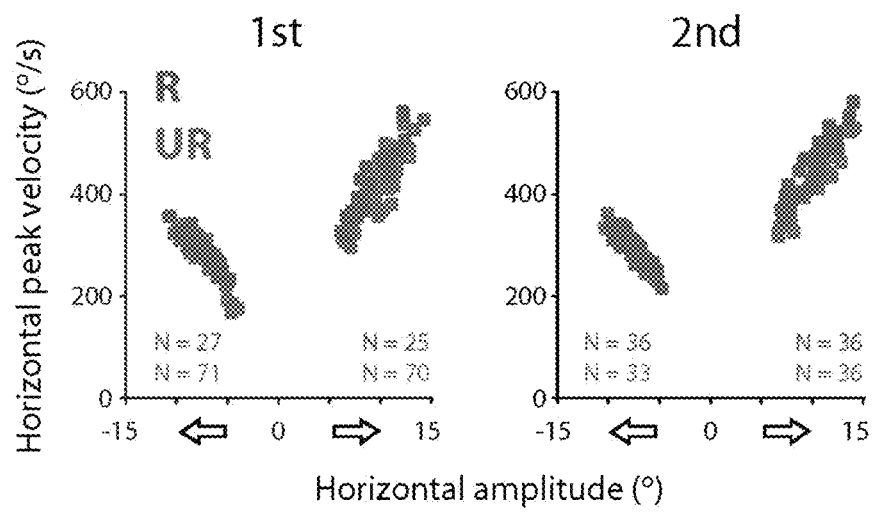

FIG. 11B plots saccadic velocities as a function of amplitudes (abscissa) for all successful saccades from the same subject. Even though there existed an intimate amplitude-velocity coupling, rewarded rightward saccades were in general faster than unrewarded rightward saccades. This apparent reward modulation persisted in both tests (first: left plot; second: right plot), confirming the impression of individual velocity traces (FIG. 11A).

Another subject's rightward (temporal) saccades were faster compared to leftward (nasal) saccades (FIG. 11B). For instance, 10° rightward saccades had a peak velocity of ~420°/s, whereas 10° leftward saccades had a relatively lower peak velocity, ~320°/s.

Quantification of Reward Modulation on Saccadic Velocities

Figure 12A:
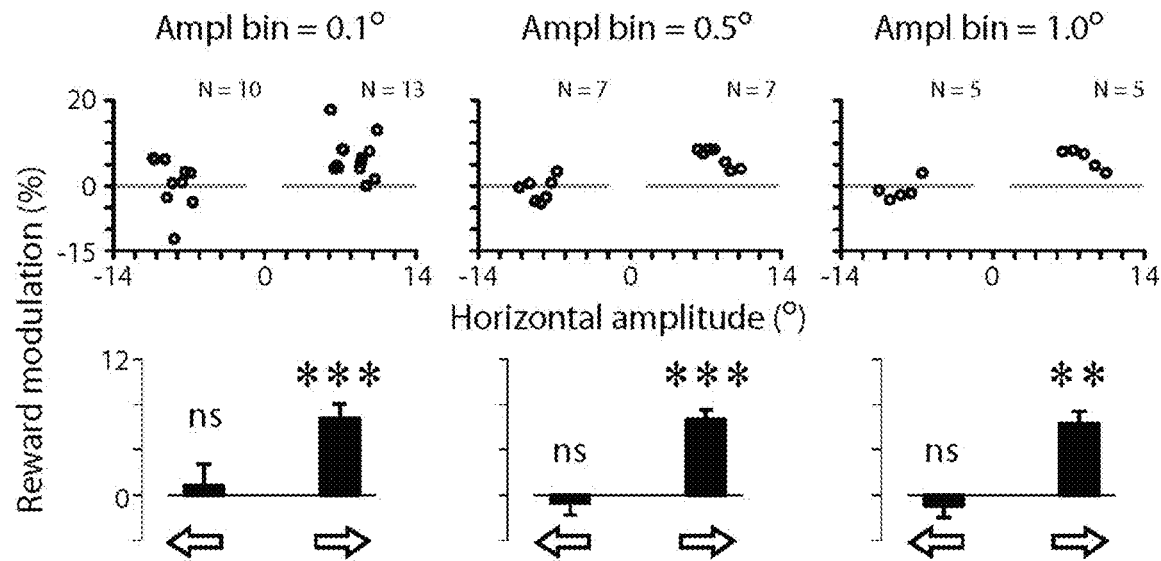
FIG. 12 includes graphs of the first tests (A) and second tests (B) showing reward modulation on saccadic velocities for subject F3 based on 3 different amplitude bin widths (0.1° (left panels), 0.5° (middle panels), and 1.0° (right panels)), where reward modulation is plotted as the percent velocity change between rewarded and unrewarded saccades across amplitude bins in scatter plots.
Figure 12B:
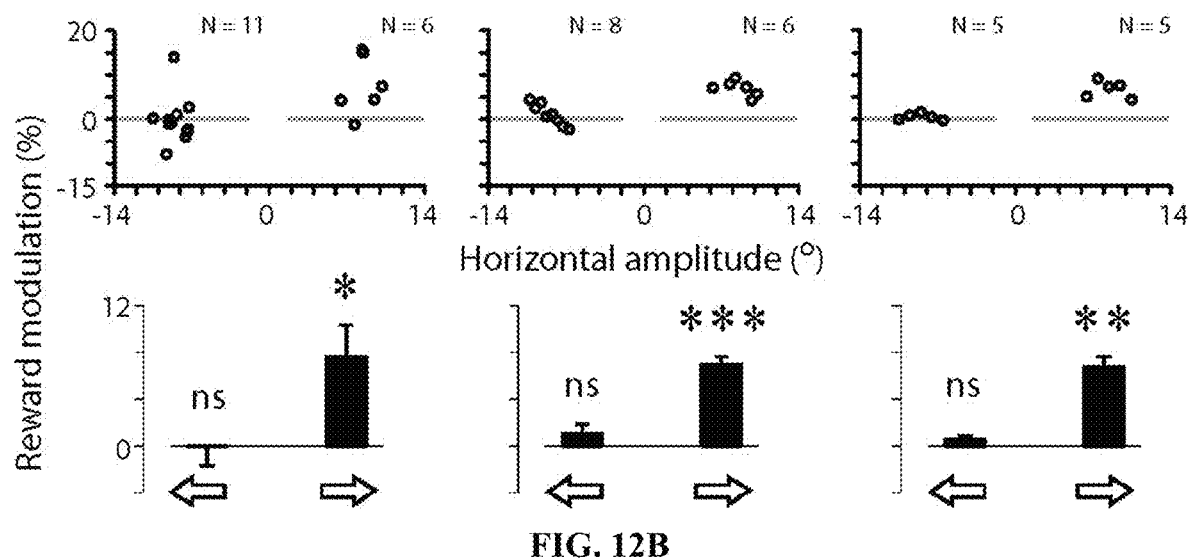

Next, it was determined how the reward modulation embedded in the main sequence could be quantified, i.e., amplitude-velocity relationship. FIG. 12 quantifies the effect of reward expectation on saccadic velocities. The scatter plots of FIG. 12 show the individual data point for each amplitude bin width (left panels: 0.1°; middle panels: 0.5°; right panels: 1.0°; see Methods). The data variance at 0.1° amplitude bin width was greater than that of 0.5° and 1.0°. In addition, the results based on bin width of 0.5° and 1.0° were in general agreement with one another. This may have been due to the fact that the eye tracker had a resolution of 0.1°, rendering noisy data analysis at 0.1° bin width. Thus, the measurement resolution may be set at >3x of that of the equipment. Based on these reasons, a 0.5° amplitude bin width was applied for the rest of the analyses.

For the subject, all data points of rightward saccades were above zero, reflecting that reward expectation significantly sped up the saccades across all amplitude bins (FIG. 12, middle scatter plots; one-sample t test, 2 tail, $P<0.001$ for both tests). In contrast, the data points of leftward saccades were distributed around zero, reflecting the lack of modulation ($P>0.05$ for both tests). The bar charts show the reward modulation separated for saccadic directions (open arrows; FIG. 12).

As can be noted in FIG. 12, a reduction of amplitude bin width did not increase proportionally the number of valid data points in the scatter plots. For example, a 10-fold reduction of amplitude bin width (from 1.0° to 0.1°) led to approximately 2-fold increase of data points (FIG. 12). This may have been because that each bin must contain both rewarded and unrewarded data to be counted as a valid data point in the plot. Hence, the number of valid data points was not increased in proportion with the decrease of bin width.

This method dissociated the modulation of saccadic velocity from saccadic amplitude, permitting the velocity modulation to be evaluated independently of saccadic amplitude and without sacrificing the amplitude sensitivity.

Figure 13A:
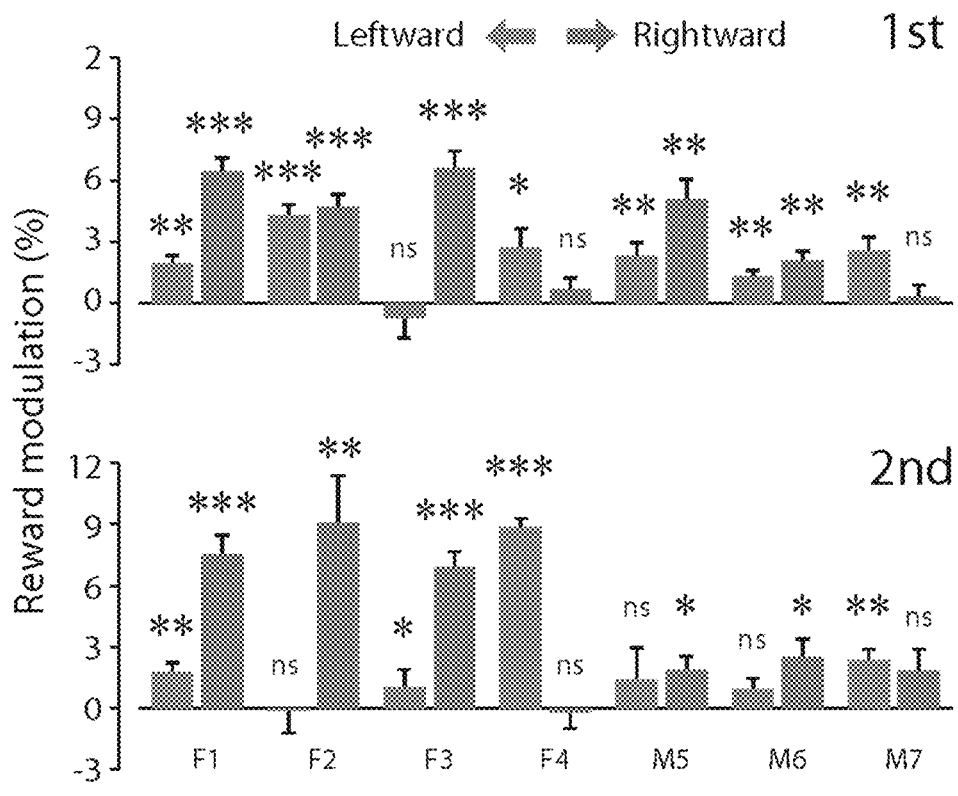
FIG. 13 includes graphs showing the average reward modulation on saccadic velocities separated for saccadic directions for (A) each subject separated for test order (first.

FIG. 13A shows the reward modulation on the saccadic velocities of individual subjects. Consider the first test (FIG. 13A, top). Reward expectation significantly sped up leftward saccades (one-sample t test, 2 tail, $P<0.05$) in all subjects (up to 4.3%) except subject F3 (−0.7%). In addition, reward expectation significantly sped up rightward saccades (one-sample t test, 2 tail, $P<0.05$) in all subjects (up to 6.6%) except subjects F4 (0.7%) and M7 (0.3%). In other words, monetary reward sped up voluntary saccades at least in one of the horizontal directions. In addition, reward modulation did not negatively impact the saccadic velocities in these subjects, consistent with the previous Examples describing nonhuman primate studies.

Similar results were obtained during the second test (FIG. 13A, bottom). Reward expectation significantly sped up leftward saccades (one-sample t test, 2 tail, $P<0.05$) in all subjects (up to 8.9%) except subjects F2 (−0.1%), M5 (−1.4%) and M6 (0.9%). In addition, reward expectation significantly sped up rightward saccades (one-sample t test, 2 tail, $P<0.05$) in all subjects (up to 9.1%) except subjects F4 (−0.2%) and M7 (1.8%). That is, monetary reward sped up saccades, even though these rewarded saccades were presumably pre-primed by a preceding unrewarded saccade.

Table 5 shows the analysis based on the peak velocity changes between rewarded and unrewarded saccades for each subject. The results of Table 5, including the level of statistical significance, were consistent with the reward percentage results obtained from FIG. 13.

TABLE 5

Reward-associated velocity modulation computed as the average peak velocity (PV) changes (mean ± S.E.M.) between rewarded and unrewarded saccades (see Methods; Eq. 2). Positive values indicate that rewarded saccades were faster than unrewarded saccades, whereas negative values, unrewarded saccades were faster than rewarded saccade.

| | Leftward Saccade | | | Rightward Saccade | | |
|---|---|---|---|---|---|---|
| | PV change (°/s) | N | P | PV change (°/s) | N | P |
| First test | | | | | | |
| F1 | 6.0 ± 1.2 | 8 | <0.01 | 25.9 ± 3.3 | 8 | <0.001 |
| F2 | 13.4 ± 1.5 | 9 | <0.001 | 16.0 ± 2.4 | 9 | <0.001 |
| F3 | −2.2 ± 2.8 | 7 | n.s. | 19.9 ± 2.1 | 7 | <0.001 |
| F4 | 9.2 ± 3.3 | 8 | <0.05 | 2.7 ± 2.2 | 9 | n.s. |
| M5 | 5.8 ± 1.6 | 9 | <0.01 | 13.5 ± 2.7 | 8 | <0.01 |
| M6 | 4.0 ± 0.8 | 9 | <0.01 | 7.6 ± 1.7 | 9 | <0.01 |
| M7 | 9.3 ± 2.1 | 9 | <0.01 | 1.4 ± 1.8 | 8 | n.s. |
| Second test | | | | | | |
| F1 | 5.5 ± 1.3 | 8 | <0.01 | 30.4 ± 3.8 | 6 | <0.001 |
| F2 | −0.1 ± 3.5 | 8 | n.s. | 33.3 ± 8.7 | 7 | <0.01 |
| F3 | 3.7 ± 2.7 | 8 | <0.05 | 22.5 ± 2.1 | 6 | <0.001 |
| F4 | 29.0 ± 2.4 | 8 | <0.001 | −0.3 ± 2.9 | 9 | n.s. |
| M5 | 3.1 ± 3.7 | 7 | n.s. | 5.0 ± 1.7 | 8 | <0.05 |
| M6 | 2.5 ± 1.5 | 9 | n.s. | 8.9 ± 3.0 | 8 | <0.05 |
| M7 | 8.5 ± 1.8 | 9 | <0.01 | 6.8 ± 3.6 | 8 | n.s. |

Figure 13B:
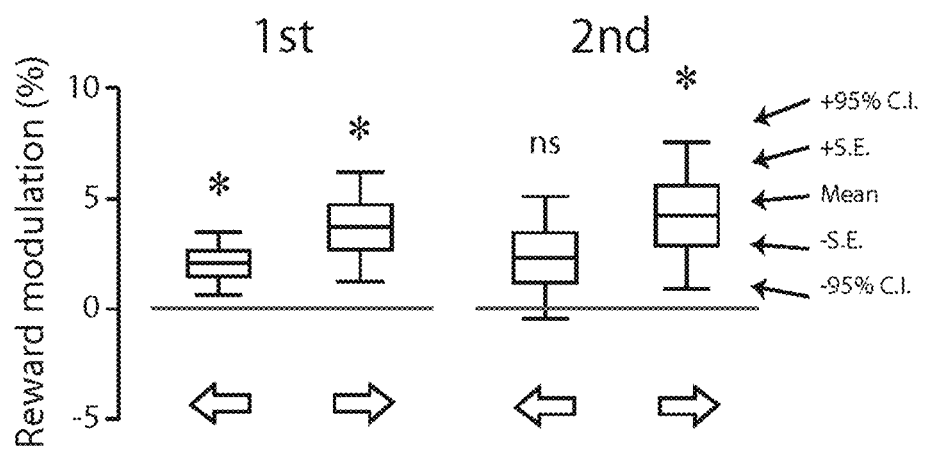

FIG. 13B shows the population summary for these subjects. The reward modulation during the first test was statistically significant for both leftward (2.1±0.6%; 6.5±1.9°/s, N=7) and rightward (3.7±1.0%; 12.4±3.4°/s, N=7) saccades (one-sample t test, $P<0.05$ for both). This indicated that the reward modulation was robust and detectable at the population averages. Nevertheless, the reward modulation during the second test was statistically significant only for rightward saccades (4.2±1.3%; 15.2±5.0°/s, N=7; $P<0.05$) and not for leftward saccades (2.3±1.1%;

7.5±3.7°/s, N=7; P>0.05). This is likely to result from increased data variance during the second test. There was no significant difference in the reward modulation between leftward and rightward saccades (2 dependent-sample t test, P>0.05 for both first and second tests). The results suggest that monetary reward speeds up saccades in human in a fashion analogous to how juice reward sped up saccades in monkeys.

FIG. 14 plots the correlation of reward modulation during the first test and that during the second test. There was a positive correlation for rightward saccades (B), whereas there was no apparent correlation for leftward saccades (A). The right eyes were recorded from these subjects and suggest that, in spite of sensorimotor priming presumably resulting from consecutive saccades, the reward modulation was relatively consistent.

Nasal-Temporal Velocity Asymmetry

Figure 15A:
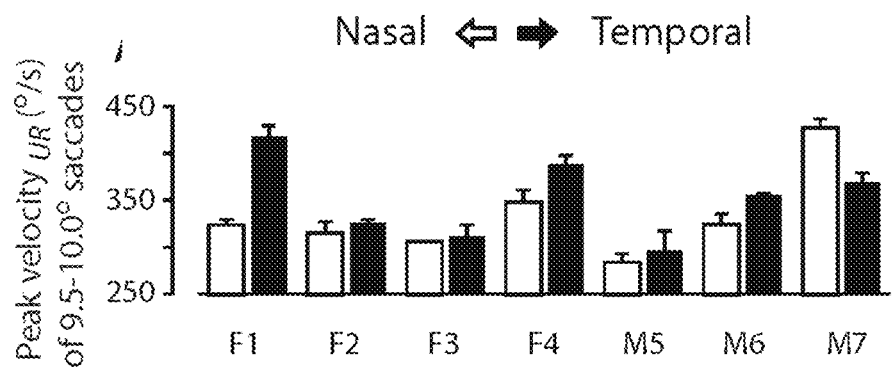

Saccadic velocities can vary for abducting (temporal) or adducting (nasal) directions. The main sequence relationship illustrated in FIG. 11B agreed with this notion. FIG. 15A shows an example of the velocity asymmetry across all subjects. The saccadic velocities were selected from 9.5-10.0° unrewarded saccades during the first test. The velocity asymmetry varied significantly across these subjects.

Figure 15B:
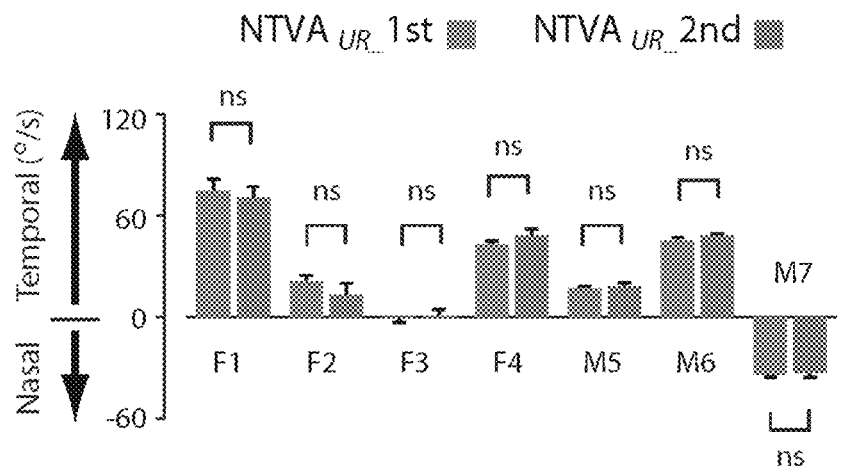

To determine how stable the velocity asymmetry was, the nasal-temporal velocity asymmetry of unrewarded saccades was plotted (FIG. 15B). Positive values indicated that temporal saccades were faster than nasal saccades (subjects F1-M6), and vice versa (subject M7). There were 3 main points in this plot. First, subject F3 showed a lack of saccadic velocity asymmetry (one-sample t test, 2 tail, P>0.05 for either of the first or second test). This characteristic persisted across the two tests (2-sample t test, 2 tail, P>0.05). Second, all other subjects showed a significant nasal-temporal velocity asymmetry. Their saccadic velocities were on average 13-75°/sec higher in the temporal or nasal direction than the opposite direction (P<0.001 for either of the first and second test). Third, this intrinsic velocity asymmetry remained unchanged across the tests (2-sample t test, 2 tail, P>0.05 for all subjects). The cross-subject average change of the velocity asymmetry between the two tests was statistically negligible (−0.0±1.7°/s, 95% confidence interval: ±9.0°/s; P>0.05).

This was consistent with the normalized measures across amplitude bins (Table 6). The normalized measures showed that the saccadic velocity asymmetry persisted regardless of test order (2-sample t test, 2 tail, P>0.05 for all subjects). The cross-subject average of this measure was also near zero (−0.1±0.6%, 95% confidence interval: ±3.1%; P>0.05).

TABLE 6

Nasal-temporal velocity asymmetry (NTVA) computed as the average percent velocity changes (mean ± S.E.M.) between temporal and nasal saccades (see Methods; Eq. 1). Positive values indicate that temporal saccades were faster than nasal saccades, whereas negative values, nasal saccades were faster than temporal saccade.

| | First test | | | Second test | | |
|---|---|---|---|---|---|---|
| | NTVA (%) | N | P | NTVA (%) | N | P |
| Unrewarded saccades | | | | | | |
| F1 | 19.7 ± 1.1 | 9 | <0.001 | 18.7 ± 1.0 | 6 | <0.001 |
| F2 | 6.8 ± 1.1 | 9 | <0.001 | 3.8 ± 2.0 | 8 | n.s. |
| F3 | −0.3 ± 0.9 | 8 | n.s. | 0.0 ± 1.2 | 7 | n.s. |
| F4 | 12.0 ± 0.6 | 9 | <0.001 | 14.0 ± 1.0 | 8 | <0.001 |

TABLE 6-continued

Nasal-temporal velocity asymmetry (NTVA) computed as the average percent velocity changes (mean ± S.E.M.) between temporal and nasal saccades (see Methods; Eq. 1). Positive values indicate that temporal saccades were faster than nasal saccades, whereas negative values, nasal saccades were faster than temporal saccade.

| | First test | | | Second test | | |
|---|---|---|---|---|---|---|
| | NTVA (%) | N | P | NTVA (%) | N | P |
| M5 | 6.9 ± 0.4 | 9 | <0.001 | 7.2 ± 0.8 | 6 | <0.001 |
| M6 | 13.2 ± 0.4 | 9 | <0.001 | 13.7 ± 0.4 | 8 | <0.001 |
| M7 | −10.5 ± 0.5 | 9 | <0.001 | −10.2 ± 0.7 | 8 | <0.001 |
| Rewarded saccades | | | | | | |
| F1 | 22.0 ± 1.3 | 7 | <0.001 | 25.9 ± 0.3 | 7 | <0.001 |
| F2 | 7.2 ± 0.5 | 9 | <0.001 | 12.7 ± 1.5 | 8 | <0.001 |
| F3 | 6.4 ± 1.0 | 6 | <0.01 | 6.1 ± 0.6 | 7 | <0.001 |
| F4 | 11.0 ± 0.9 | 9 | <0.001 | 7.9 ± 0.5 | 8 | <0.001 |
| M5 | 9.4 ± 0.8 | 8 | <0.001 | 7.2 ± 0.9 | 9 | <0.001 |
| M6 | 13.9 ± 0.3 | 9 | <0.001 | 14.4 ± 0.5 | 9 | <0.001 |
| M7 | −13.7 ± 1.6 | 8 | <0.001 | −10.6 ± 1.1 | 9 | <0.001 |

Figure 15C:
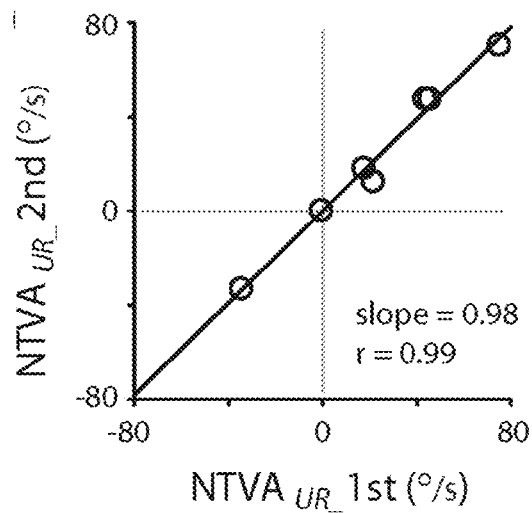

FIG. 15C shows the correlation of the nasal-temporal velocity asymmetry between the first (abscissa) and second (ordinate) tests. There was a nearly 1-to-1 correlation between the repeated measures of the velocity asymmetry of unrewarded saccades (Pearson correlation, r=0.99, P<0.001), suggesting that this velocity asymmetry was highly stable.

Figure 16A:
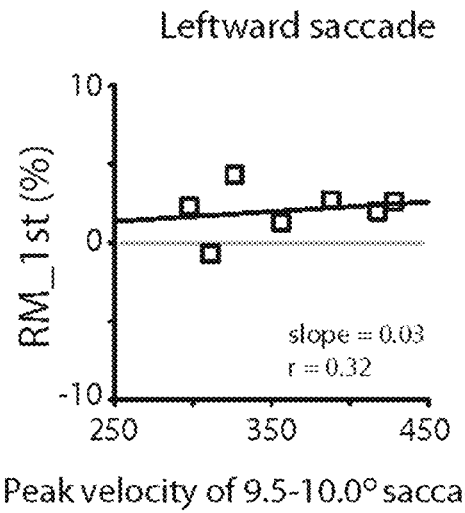
Figure 16B:
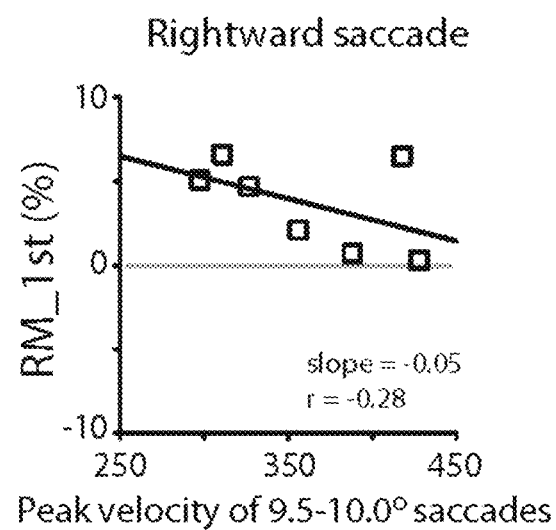

Next, it was determined whether the variability of peak velocities of unrewarded saccades or the magnitude of the intrinsic velocity asymmetry predicts the magnitude of reward modulation on saccadic velocity. FIG. 16 plots the correlation between these variables, separated for leftward (A, C and E) and rightward (B, D and F) saccades. There was no apparent relationship between the peak velocities of a given amplitude of saccades, 9.5-10.0° in this case, and the reward modulation during the first test (Pearson correlation, P>0.05 for both leftward and rightward saccades; FIGS. 16A and 16B) or during the second test (slope=0.02, r=0.39, for leftward saccades; slope=−0.01, r=−0.21 for rightward saccades; P>0.05 for both; data not shown). In other words, the subjects' tendency to make faster or slower saccades was not correlated with higher or lower reward modulation on saccadic velocity.

Figure 16C:
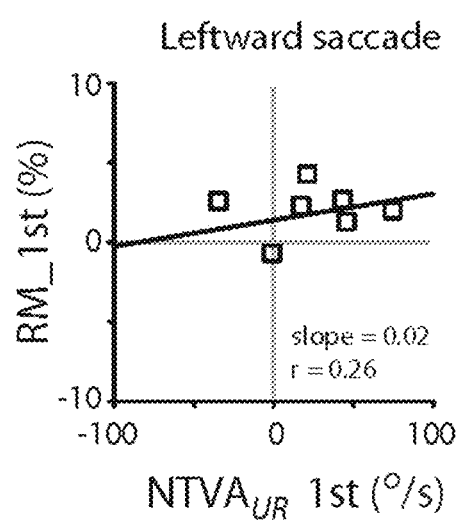
Figure 16D:
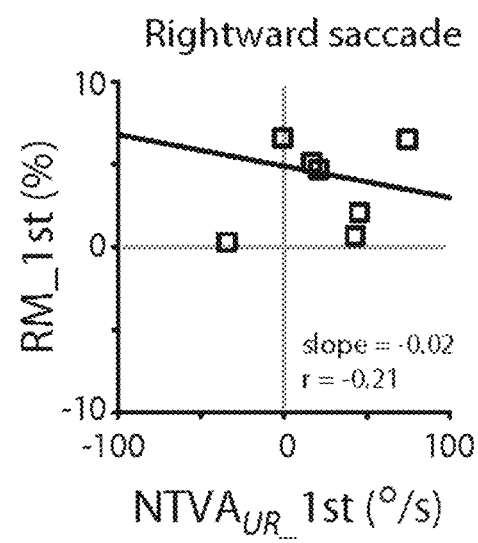
Figure 16E:
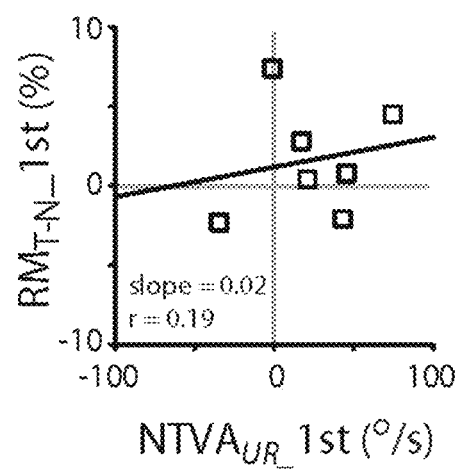
Figure 16F:
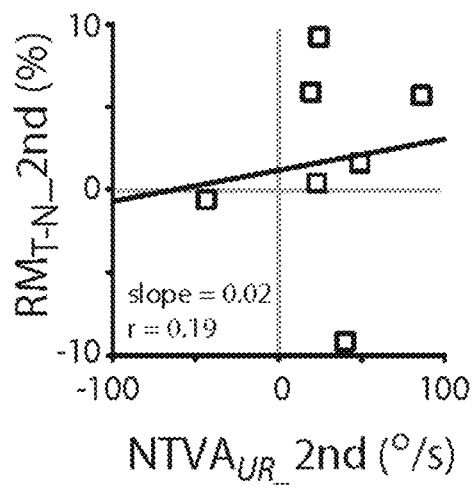

There was no apparent relationship between the magnitude of the nasal-temporal asymmetry and the reward modulation during the first test (Pearson correlation, P>0.05; FIGS. 16C and 16D) or during the second test (slope=0.03, r=0.26, for leftward saccades; slope=−0.01, r=−0.07 for rightward saccades; P>0.05 for both; data not shown). In addition, there was no apparent relationship between the magnitude of the nasal-temporal asymmetry and the differential reward modulation between temporal saccades and nasal saccades, either during the first or second test (Pearson correlation, P>0.05; FIGS. 16E and 16F). That is, the magnitude of subjects' intrinsic velocity asymmetry was not correlated with the reward modulation on saccadic velocity.

Thus, the results suggest that the nasal-temporal velocity asymmetry was a unique, built-in characteristic, that was present regardless of whether the saccades were reflexive or voluntary. This suggests that the control may be intrinsic to the saccade generator or is regulated by the structures utilized by both reflexive and voluntary saccades, for instance, at the level of or downstream from the superior colliculus. This finding is consistent with the finding that velocity asymmetry was highly stable across the test order, i.e., resistant to the sensorimotor modulations that occurred across series of saccades (FIG. 15B). This was also in agreement with the finding that velocity asymmetry is resistant to reward modulation (FIGS. 16C and 16D).

While the terms used herein are believed to be well understood by one of ordinary skill in the art, the definitions set forth herein are provided to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "an eye" includes a plurality of such eyes, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

REFERENCES

Throughout this document, various references are mentioned. All such references, including those listed below, are incorporated herein by reference.

Amador, N., Schlag-Rey, M. & Schlag, J. (2000) Reward-predicting and reward-detecting neuronal activity in the primate supplementary eye field. J. Neurophysiol., 84, 2166-2170.

Amador, N., Schlag-Rey, M. & Schlag, J. (2004) Primate antisaccade. II. Supplementary eye field neuronal activity predicts correct performance. J. Neurophysiol., 91, 1672-1689.

Bahill, A. T., Clark, M. R., and Stark, L. (1975). The main sequence, a tool for studying human eye movements. *Math Biosci.* 24, 191-204.

Baloh, R. W., Sills, A. W., Kumley, W. E., and Honrubia, V. (1975). Quantitative measurement of saccade amplitude, duration, and velocity. *Neurology* 25, 1065-1070.

Barton, E. J. & Sparks, D. L. (2001) Saccades to remembered targets exhibit enhanced orbital position effects in monkeys. Vision Res., 41, 2393-2406.

Basso, M. A. & Sommer, M. A. (2011) Exploring the role of the substantia nigra pars reticulata in eye movements. Neuroscience, 198, 205-212.

Bray, S. and O'Doherty, J. (2007). Neural coding of reward-prediction error signals during classical conditioning with attractive faces. *J. Neurophysiol.* 97, 3036-3045, doi: 01211.2006 [pii]; 10.1152/jn.01211.2006 [doi].

Bromberg-Martin, E. S. and Hikosaka, O. (2009). Midbrain dopamine neurons signal preference for advance information about upcoming rewards. *Neuron* 63, 119-126.

Chen, L. L. (2006) Head movements evoked by electrical stimulation in the frontal eye field of the monkey: evidence for independent eye and head control. J. Neurophysiol., 95, 3528-3542.

Chen, L. L. & Tehovnik, E. J. (2007) Cortical control of eye and head movements: integration of movements and percepts. Eur. J. Neurosci., 25, 1253-1264.

Chen, L. L. & Walton, M. M. (2005) Head movement evoked by electrical stimulation in the supplementary eye field of the rhesus monkey. J. Neurophysiol., 94, 4502-4519.

Chen, L. L. & Wise, S. P. (1995a) Neuronal activity in the supplementary eye field during acquisition of conditional oculomotor associations. J. Neurophysiol., 73, 1101-1121.

Chen, L. L. & Wise, S. P. (1995b) Supplementary eye field contrasted with the frontal eye field during acquisition of conditional oculomotor associations. J. Neurophysiol., 73, 1122-1134.

Chen, L. L. & Wise, S. P. (1996) Evolution of directional preferences in the supplementary eye field during acquisition of conditional oculomotor associations. J. Neurosci., 16, 3067-3081.

Chen, L. L. & Wise, S. P. (1997) Conditional oculomotor learning: population vectors in the supplementary eye field. J. Neurophysiol., 78, 1166-1169.

Chen, L. L., Hung, L. Y., Quinet, J., and Kosek, K. (2013). Cognitive regulation of saccadic velocity by reward prospect. *Eur. J. Neurosci.* 38, 2434-2444.

Collewijn, H., Erkelens, C. J. & Steinman, R. M. (1988) Binocular co-ordination of human horizontal saccadic eye movements. J. Physiol., 404, 157-182.

Collins, C. C., O'Meara, D. & Scott, A. B. (1975) Muscle tension during unrestrained human eye movements. J. Physiol., 245, 351-369.

Davis-Lopez de Carrizosa, M. A., Morado-Diaz, C. J., Miller, J. M., de la Cruz, R. R. & Pastor, A. M. (2011) Dual encoding of muscle tension and eye position by abducens motoneurons. J. Neurosci., 31, 2271-2279.

Ding, L. & Hikosaka, O. (2006) Comparison of reward modulation in the frontal eye field and caudate of the macaque. J. Neurosci., 26, 6695-6703.

Fahle, M. and Schmid, M. (1988). Naso-temporal asymmetry of visual perception and of the visual cortex. *Vision Res.* 28, 293-300.

Fuchs, A. F. & Robinson, D. A. (1966) A method for measuring horizontal and vertical eye movement chronically in the monkey. J. Appl. Physiol., 21, 1068-1070.

Gamlin, P. D. & Miller, J. M. (2012) Extraocular muscle motor units characterized by spike-triggered averaging in alert monkey. J. Neurosci. Meth., 204, 159-167.

Glimcher, P. W. (2011) Understanding dopamine and reinforcement learning: the dopamine reward prediction error hypothesis. Proc. Natl. Acad. Sci. USA, 108(Suppl3), 15647-15654.

Gregorios-Pippas, L., Tobler, P. N., and Schultz, W. (2009). Short-term temporal discounting of reward value in human ventral striatum. J. Neurophysiol. 101, 1507-1523.

Haith, A. M., Reppert, T. R. & Shadmehr, R. (2012) Evidence for hyperbolic temporal discounting of reward in control of movements. J. Neurosci., 32, 11727-11736.

Hanes, D. P., Smith, M. K., Optican, L. M. & Wurtz, R. H. (2005) Recovery of saccadic dysmetria following localized lesions in monkey superior colliculus. Exp. Brain Res., 160, 312-325.

Hayden, B. Y., Parikh, P. C., Deaner, R. O. and Platt, M. L. (2007). Economic principles motivating social attention in humans. Proc. Biol. Sci. 274, 1751-1756, doi: 3465J3457K7L6620 [pii]; 10.1098/rspb.2007.0368 [doi].

Hikosaka, O., Nakamura, K., and Nakahara, H. (2006). Basal ganglia orient eyes to reward. J. Neurophysiol. 95, 567-584.

Hikosaka, O. & Wurtz, R. H. (1983) Visual and oculomotor functions of monkey substantia nigra pars reticulata. IV. Relation of substantia nigra to superior colliculus. J. Neurophysiol., 49, 1285-1301.

Hikosaka, O. & Wurtz, R. H. (1985a) Modification of saccadic eye movements by GABA-related substances. I. Effect of muscimol and bicuculline in monkey superior colliculus. J. Neurophysiol., 53, 266-291.

Hikosaka, O. & Wurtz, R. H. (1985b) Modification of saccadic eye movements by GABA-related substances. II. Effects of muscimol in monkey substantia nigra pars reticulata. J. Neurophysiol., 53, 292-308.

Hikosaka, O., Takikawa, Y. & Kawagoe, R. (2000) Role of the basal ganglia in the control of purposive saccadic eye movements. Physiol. Rev., 80, 953-978.

Hong, S. & Hikosaka, O. (2011) Dopamine-mediated learning and switching in cortico-striatal circuit explain behavioral changes in reinforcement learning. Front. Behav. Neurosci., 5, 15.

Isoda, M. & Hikosaka, O. (2011) Cortico-basal ganglia mechanisms for overcoming innate, habitual and motivational behaviors. Eur. J. Neurosci., 33, 2058-2069.

Itoh, H., Nakahara, H., Hikosaka, O., Kawagoe, R., Takikawa, Y. & Aihara, K. (2003) Correlation of primate caudate neural activity and saccade parameters in reward-oriented behavior. J. Neurophysiol., 89, 1774-1783.

Johannesson, O. I., Asgeirsson, A. G., and Kristjansson, A. (2012). Saccade performance in the nasal and temporal hemifields. Exp. Brain Res. 219, 107-120, doi:10.1007/s00221-012-3071-2 [doi].

Judge, S. J., Richmond, B. J. & Chu, F. C. (1980) Implantation of magnetic search coils for measurement of eye position: an improved method. Vision Res., 20, 535-538.

Kable, J. W. and Glimcher, P. W. (2007). The neural correlates of subjective value during intertemporal choice. Nat. Neurosci 10, 1625-1633.

Kable, J. W. and Glimcher, P. W. (2010). An "as soon as possible" effect in human intertemporal decision making: behavioral evidence and neural mechanisms. J. Neurophysiol. 103, 2513-2531.

Kampe, K. K., Frith, C. D., Dolan, R. J., and Frith, U. (2001). Reward value of attractiveness and gaze. Nature 413, 589, doi:10.1038/35098149 [doi]; 35098149 [pii].

Kato, M., Miyashita, N., Hikosaka, O., Matsumura, M., Usui, S. & Kori, A. (1995) Eye movements in monkeys with local dopamine depletion in the caudate nucleus. I. Deficits in spontaneous saccades. J. Neurosci., 15, 912-927.

Kawagoe, R., Takikawa, Y. & Hikosaka, O. (1998) Expectation of reward modulates cognitive signals in the basal ganglia. Nat. Neurosci., 1, 411-416.

Kawagoe, R., Takikawa, Y. & Hikosaka, O. (2004) Reward-predicting activity of dopamine and caudate neurons—a possible mechanism of motivational control of saccadic eye movement. J. Neurophysiol., 91, 1013-1024.

Kobayashi, S. and Schultz, W. (2008). Influence of reward delays on responses of dopamine neurons. J. Neurosci. 28, 7837-7846.

Koene, A. R. & Erkelens, C. J. (2002) Cause of kinematic differences during centrifugal and centripetal saccades. Vision Res., 42, 1797-1808.

Kustov, A. A. & Robinson, D. L. (1995) Modified saccades evoked by stimulation of the macaque superior colliculus account for properties of the resettable integrator. J. Neurophysiol., 73, 1724-1728.

Lee, C., Rohrer, W. H. & Sparks, D. L. (1988) Population coding of saccadic eye movements by neurons in the superior colliculus. Nature, 332, 357-360.

Lefevre, P., Quaia, C. & Optican, L. M. (1998) Distributed model of control of saccades by superior colliculus and cerebellum. Neural Networks, 11, 1175-1190.

Levy, D. J. & Glimcher, P. W. (2012) The root of all value: a neural common currency for choice. Curr. Opin. Neurobiol., 22, 1027-1038.

Louie, K., Grattan, L. E., and Glimcher, P. W. (2011). Reward value-based gain control: divisive normalization in parietal cortex. J. Neurosci 31, 10627-10639, doi:31/29/10627 [pii];10.1523/JNEUROSCI.1237-11.2011 [doi].

Madelain, L., Paeye, C., and Wallman, J. (2011). Modification of saccadic gain by reinforcement. J. Neurophysiol. 106, 219-232, doi:jn.01094.2009 [pii]; 10.1152/jn.01094.2009 [doi].

Marino, R. A. & Munoz, D. P. (2009) The effects of bottom-up target luminance and top-down spatial target predictability on saccadic reaction times. Exp. Brain Res., 197, 321-335.

Marino, R. A., Levy, R., Boehnke, S., White, B. J., Itti, L. & Munoz, D. P. (2012) Linking visual response properties in the superior colliculus to saccade behavior. Eur. J. Neurosci., 35, 1738-1752.

Matsumoto, M. & Hikosaka, O. (2009) Two types of dopamine neuron distinctly convey positive and negative motivational signals. Nature, 459, 837-841.

May, P. J. (2006) The mammalian superior colliculus: laminar structure and connections. Prog. Brain Res., 151, 321-378.

McClure, S. M., Ericson, K. M., Laibson, D. I., Loewenstein, G., and Cohen, J. D. (2007). Time discounting for primary rewards. J. Neurosci. 27, 5796-5804.

Meyer, G. A., McCulloch, A. D. & Lieber, R. L. (2011) A nonlinear model of passive muscle viscosity. J. Biomech. Eng., 133, 091007.

Miller, J. M., Pavlovski, D. S. & Shamaeva, I. (2009) Orbit 1.8 Gaze mechanics simulation. Eidactics, San Francisco.

Miller, J. M., Davison, R. C. & Gamlin, P. D. (2011) Motor nucleus activity fails to predict extraocular muscle forces in ocular convergence. J. Neurophysiol., 105, 2863-2873.

Nakamura, K. & Hikosaka, O. (2006) Role of dopamine in the primate caudate nucleus in reward modulation of saccades. J. Neurosci., 26, 5360-5369.

Nichols, M. J. & Sparks, D. L. (1995) Nonstationary properties of the saccadic system: new constraints on models of saccadic control. J. Neurophysiol., 73, 431-435.

Nichols, M. J. & Sparks, D. L. (1996) Component stretching during oblique stimulation-evoked saccades: the role of the superior colliculus. J. Neurophysiol., 76, 582-600.

van Opstal, A. J. & van Gisbergen, J. A. (1990) Role of monkey superior colliculus in saccade averaging. Exp. Brain Res., 79, 143-149.

van Opstal, A. J., Hepp, K., Suzuki, Y. & Henn, V. (1995) Influence of eye position on activity in monkey superior colliculus. J. Neurophysiol., 74, 1593-1610.

Optican, L. M. & Quaia, C. (2002) Distributed model of collicular and cerebellar function during saccades. Ann. NY Acad. Sci., 956, 164-177.

Pare, M. & Munoz, D. P. (1996) Saccadic reaction time in the monkey: advanced preparation of oculomotor programs is primarily responsible for express saccade occurrence. J. Neurophysiol., 76, 3666-3681.

Pasupathy, A. and Miller, E. K. (2005). Different time courses of learning-related activity in the prefrontal cortex and striatum. *Nature* 433, 873-876.

Pelisson, D. & Prablanc, C. (1988) Kinematics of centrifugal and centripetal saccadic eye movements in man. Vision Res., 28, 87-94.

Pfann, K. D., Keller, E. L. & Miller, J. M. (1995) New models of the oculomotor mechanics based on data obtained with chronic muscle force transducers. Ann. Biomed. Eng., 23, 346-358.

Quaia, C. & Optican, L. M. (1997) Model with distributed vectorial premotor bursters accounts for the component stretching of oblique saccades. J. Neurophysiol., 78, 1120-1134.

Quaia, C., Lefevre, P. & Optican, L. M. (1999) Model of the control of saccades by superior colliculus and cerebellum. J. Neurophysiol., 82, 999-1018.

Rafal, R., Henik, A., and Smith, J. (1991). Extrageniculate contributions to reflex visual orienting in normal humans: a temporal hemifield advantage. *J. Cogn Neurosci.* 3, 322-328.

Reulen, J. P., Marcus, J. T., Koops, D., de Vries, F. R., Tiesinga, G., Boshuizen, K., and Bos, J. E. (1988). Precise recording of eye movement: the IRIS technique. Part 1. *Med. Biol. Eng Comput.* 26, 20-26.

Robinson, D. A. (1964). The mechanics of human saccadic eye movement. *J. Physiol* 174, 245-264.

Rodriguez, C. A., Turner, B. M., and McClure, S. M. (2014). Intertemporal choice as discounted value accumulation. *PLoS. One.* 9, e90138.

Sato, M. & Hikosaka, O. (2002) Role of primate substantia nigra pars reticulata in reward-oriented saccadic eye movement. J. Neurosci., 22, 2363-2373.

Schiller, P. H., True, S. D. & Conway, J. L. (1980) Deficits in eye movements following frontal eye-field and superior colliculus ablations. J. Neurophysiol., 44, 1175-1189.

Schultz, W. (2002) Getting formal with dopamine and reward. Neuron, 36, 241-263.

Schultz, W. (2013). Updating dopamine reward signals. *Curr. Opin. Neurobiol.* 23, 229-238.

Schultz, W. (2006) Behavioral theories and the neurophysiology of reward. Annu. Rev. Psychol., 57, 87-115.

Schultz, W., Dayan, P. & Montague, P. R. (1997) A neural substrate of prediction and reward. Science, 275, 1593-1599.

Shadmehr, R. & Wise, S. P. (2005) The Computational Neurobiology of Reaching and Pointing, A Foundation for Motor Learning. The MIT Press, Cambridge, Mass.

Shadmehr, R., Orban de Xivry, J. J., Xu-Wilson, M. & Shih, T. Y. (2010) Temporal discounting of reward and the cost of time in motor control. J. Neurosci., 30, 10507-10516.

Shadmehr, R. (2010). Control of movements and temporal discounting of reward. *Curr. Opin. Neurobiol.* 20, 726-730, doi:S0959-4388(10)00137-6 [pii]; 10.1016/j.conb.2010.08.017 [doi].

Snedecor, G. W. & Cochran, W. G. (1989) Statistical Methods, 8th ed. Iowa State University Press/AMES, Iowa.

Soetedjo, R., Kaneko, C. R. & Fuchs, A. F. (2002) Evidence that the superior colliculus participates in the feedback control of saccadic eye movements. J. Neurophysiol., 87, 679-695.

Sommer, M. A. & Wurtz, R. H. (2008) Brain circuits for the internal monitoring of movements. Annu Rev. Neurosci., 31, 317-338.

Sparks, D. L. (2002) The brainstem control of saccadic eye movements. Nat. Rev. Neurosci., 3, 952-964.

Stanford, T. R. & Sparks, D. L. (1994) Systematic errors for saccades to remembered targets: evidence for a dissociation between saccade metrics and activity in the superior colliculus. Vision Res., 34, 93-106.

Sylvester, R., Josephs, O., Driver, J., and Rees, G. (2007). Visual fMRI responses in human superior colliculus show a temporal-nasal asymmetry that is absent in lateral geniculate and visual cortex. *J. Neurophysiol.* 97, 1495-1502.

Takikawa, Y., Kawagoe, R., Itoh, H., Nakahara, H. & Hikosaka, O. (2002) Modulation of saccadic eye movements by predicted reward outcome. Exp. Brain Res., 142, 284-291.

Tanaka, M. (2007) Spatiotemporal properties of eye position signals in the primate central thalamus. Cereb. Cortex, 17, 1504-1515.

Tobler, P. N., Fiorillo, C. D. & Schultz, W. (2005) Adaptive coding of reward value by dopamine neurons. Science, 307, 1642-1645.

van den Bos, W. and McClure, S. M. (2013). Towards a general model of temporal discounting. *J. Exp. Anal. Behav.* 99, 58-73.

van der Vegt, J. P., Hulme, O. J., Zittel, S., Madsen, K. H., Weiss, M. M., Buhmann, C., Bloem, B. R., Munchau, A., and Siebner, H. R. (2013). Attenuated neural response to gamble outcomes in drug-naive patients with Parkinson's disease. *Brain* 136, 1192-1203.

van Opstal, A. J., Hepp, K., Suzuki, Y., and Henn, V. (1995). Influence of eye position on activity in monkey superior colliculus. *J. Neurophysiol.* 74, 1593-1610.

van Opstal, A. J. and van Gisbergen, J. A. (1990). Role of monkey superior colliculus in saccade averaging. *Exp. Brain Res.* 79, 143-149.

Watanabe, M. & Munoz, D. P. (2011) Probing basal ganglia functions by saccade eye movements. Eur. J. Neurosci., 33, 2070-2090.

White, B. J., Theeuwes, J. & Munoz, D. P. (2012) Interaction between visual- and goal-related neuronal signals on the trajectories of saccadic eye movements. J. Cognitive Neurosci., 24, 707-717.

Wise, S. P., Chen, L. L. & Dominey, P. F. (1996) Neuronal activity during associative motor learning. In Ito, M. & Miyashita, Y. (Eds), Integrative and Molecular Approaches to Brain Function. Elservier Science Publisher, Tokyo, pp. 271-283.

Wurtz, R. H. & Goldberg, M. E. (1972) Activity of superior colliculus in behaving monkey. IV. Effects of lesions on eye movements. J. Neurophysiol., 35, 587-596.

Xu-Wilson, M., Zee, D. S., and Shadmehr, R. (2009). The intrinsic value of visual information affects saccade velocities. *Exp. Brain Res.* 196, 475-481.

Yasuda, M., Yamamoto, S. & Hikosaka, O. (2012) Robust representation of stable object values in the oculomotor Basal Ganglia. J. Neurosci., 32,16917-16932.

What is claimed is:

1. A method for identifying a level of a neurotransmitter in a subject, comprising:
displaying to the subject, on a display, a fixation point;
providing an instructional, conditional stimulus to the subject;
simultaneously displaying to the subject, on the display, a reward target and a non-reward target;
measuring a non-reward saccade movement parameter of the subject from the fixation point to the non-reward target and a reward saccade movement parameter of the subject from the fixation point to the reward target;
determining a saccade movement parameter reward modulation, the saccade movement parameter reward modulation being equal to a difference between the reward saccade movement parameter measurement and the non-reward saccade movement parameter measurement;
comparing the saccade movement parameter reward modulation of the subject to a reference saccade movement parameter reward modulation; and
identifying the level of the neurotransmitter in the subject based upon the comparing of the saccade movement parameter reward modulation of the subject and the reference saccade movement parameter reward modulation;
wherein, in the identifying step, a processor executing a software program determines when there is a statistically measurable difference between the reward modulation of the subject and the reference reward modulation, and in the identifying step the subject includes a deficiency of the neurotransmitter if the reward modulation of the subject is statistically lower than the reference reward modulation;
wherein one or both of the measuring steps are performed with a camera configured to track the reward saccade movement parameter; and
further comprising diagnosing the subject with a neurodegenerative condition if the subject includes the deficiency of the neurotransmitter.

2. The method of claim 1, wherein the saccade movement parameter is selected from a saccade velocity, a saccade amplitude, a saccade reaction time, and a combination thereof.

3. The method of claim 1, wherein the reward saccade and the non-reward saccade include a predetermined amplitude.

4. The method of claim 1, wherein the reference reward modulation is equal to a difference between a reward saccade and a non-reward saccade produced by one or more healthy subjects.

5. The method of claim 4, wherein the one or more healthy subjects include the subject after having undergone treatment for a neurodegenerative condition, the subject before contracting a neurodegenerative condition, another subject known to be healthy, or a combination thereof.

6. A method for identifying a level of a neurotransmitter in a subject, comprising:
displaying to the subject, on a display, a fixation point;
providing an instructional, conditional stimulus to the subject;
simultaneously displaying to the subject, on the display, a reward target and a non-reward target;
measuring a non-reward saccade movement parameter of the subject from the fixation point to the non-reward target and a reward saccade movement parameter of the subject from the fixation point to the reward target;
determining a saccade movement parameter reward modulation, the saccade movement parameter reward modulation being equal to a difference between the reward saccade movement parameter measurement and the non-reward saccade movement parameter measurement;
comparing the saccade movement parameter reward modulation of the subject to a reference saccade movement parameter reward modulation; and
identifying the level of the neurotransmitter in the subject based upon the comparing of the saccade movement parameter reward modulation of the subject and the reference saccade movement parameter reward modulation;
wherein, in the identifying step, a processor executing a software program determines when there is a statistically measurable difference between the reward modulation of the subject and the reference reward modulation, and determining if the subject includes an excess of the neurotransmitter if the reward modulation of the subject is statistically greater than the reference reward modulation;
wherein one or both of the measuring steps are performed with a camera configured to track the reward saccade movement parameter; and
diagnosing the subject with a condition if the subject includes the excess of the neurotransmitter.

7. The method of claim 1, wherein the neurotransmitter includes dopamine and the neurodegenerative condition includes Parkinson's disease.

8. The method of claim 7, further comprising administering a composition for treating Parkinson's disease if the subject is diagnosed as having Parkinson's disease.

9. The system of claim 1, wherein the reward target is selected from a monetary item, a food item, an item that indicates social status, or a combination thereof.

10. The method of claim 1, wherein the display is a virtual reality headset.

11. The method of claim 1, wherein the step of providing a conditional stimulus to the subject comprises displaying to the subject, on the display, an instruction to perform a saccade towards the reward target or the non-reward target.

12. The method of claim 6, wherein the neurotransmitter includes dopamine and the condition with an excess level of dopamine.

* * * * *